US008188214B2

(12) United States Patent
Schlom et al.

(10) Patent No.: US 8,188,214 B2
(45) Date of Patent: May 29, 2012

(54) BRACHYURY POLYPEPTIDES AND METHODS FOR USE

(75) Inventors: Jeffrey Schlom, Potomac, MD (US); Claudia M. Palena, Rockville, MD (US); Andrei P. Kozlov, St. Petersburg (RU); Kwong-yok Tsang, Bethesda, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 143 days.

(21) Appl. No.: 12/528,796

(22) PCT Filed: Feb. 27, 2008

(86) PCT No.: PCT/US2008/055185
§ 371 (c)(1),
(2), (4) Date: Aug. 26, 2009

(87) PCT Pub. No.: WO2008/106551
PCT Pub. Date: Sep. 4, 2008

(65) Prior Publication Data
US 2010/0055121 A1 Mar. 4, 2010

Related U.S. Application Data

(60) Provisional application No. 60/904,236, filed on Feb. 28, 2007.

(51) Int. Cl.
C07K 5/00 (2006.01)
A61K 38/00 (2006.01)
A61K 39/00 (2006.01)
C12N 15/00 (2006.01)
C07H 21/04 (2006.01)

(52) U.S. Cl. ........ 530/300; 536/23.5; 514/2; 435/320.1; 424/184.1; 424/185.1

(58) Field of Classification Search .................. None
See application file for complete search history.

(56) References Cited

U.S. PATENT DOCUMENTS

| | | | |
|---|---|---|---|
| 6,001,349 A | 12/1999 | Panicali et al. | |
| 6,849,255 B2 * | 2/2005 | Gazit et al. | 424/93.21 |
| 6,893,869 B2 | 5/2005 | Schlom et al. | |
| 7,052,703 B1 | 5/2006 | Pastan et al. | |
| 7,115,361 B2 | 10/2006 | Lalvani et al. | |
| 7,118,738 B2 | 10/2006 | Schlom et al. | |
| 7,211,432 B2 | 5/2007 | Schlom et al. | |

FOREIGN PATENT DOCUMENTS

| | | |
|---|---|---|
| WO | WO 02/103028 | 12/2002 |
| WO | WO 2004/030615 * | 4/2004 |

OTHER PUBLICATIONS

Score sequence search, UniProt database, "20110718_154449_us-12-528-796-3subl.rup" Jul. 18, 2011, 9 pages.*

Ausubel et al (Current Protocols in molecular Biology, 1995, 3rd edition, Wiley & Sons, NY, Section 9, p. 9-1 to 9-14).*
Edwards et al (Genome Research, 1996, 6:226-233).*
Score sequence search, Geneseq database, "20110718_154449_us-12-528-796-3subl.rag" Jul. 18, 2011; 8 pages.*
Arlen et al., "Pox viral vaccine approaches," Abstract, *Semin Oncol.* 32: 549-555 (2005).
Barnova et al., "In silico screening for tumor-specific expressed sequences in human genome," *FEBS Letters* 508:143-148 (2001).
Database EMBL, Accession No. DD387143 (Jan. 24, 2007).
Database WPI Week 200432, "New Tumor-Associated Target Polypeptides and Nucleic Acids, Useful in Preparing a Medicament for Treating or Detecting a Proliferation Disorder, E.G. Breast, Lung, Colorectal, Ovarian or Prostate Cancer or Tumor," Abstract, *Thomson Scientific*, London, GB; AN; 2004-347921, sequences 2135 and 2136 (Apr. 15, 2004).
GenBank Accession No. AF012131, Jan. 1, 1998.
Gokhale et al., "Brachyury is Expressed by Human Teratocarcinoma Cells in the Absence of Mesodermal Differentiation," *Cell Growth Differ* 11: 157-162 (2000).
International Search report for PCT Application No. PCT/US2008/055185, 6 pages (Jan. 19, 2009).
Palena et al., The Human T-Box Mesodermal Transcription Factor Brachyury is a Candidate Target for T-Cell-Mediated Cancer Immunotherapy, *Clin. Cancer Res*. 13(8):2471-2478 (2007).
Romeo and Hogendoorn, "Brachyury and chordoma: the chondroid-chordoid dilemma resolved," *Journal of Pathology* 209: 143-146 (2006).
Stan et al., "DNA Vaccines Against Cancer," *Hematol Oncol Clin N Am* 20: 613-636 (2006). Vujovic et al., "Bachyury, a crucial regulator of notochordal development, is a novel biomarker for chordomas," *Journal of Pathology* 209:157-165 (2006).
Vujovic et al., "Microarray analysis of mesenchymal tumors identifiers brachyury, a novel biomarker for chordomas," *Journal of Pathology* 210(S):1 (2006).

* cited by examiner

*Primary Examiner* — Laura B Goddard
(74) *Attorney, Agent, or Firm* — Klarquist Sparkman, LLP

(57) ABSTRACT

It is disclosed herein that Brachyury is expressed in human tumors, specifically in tumors of the small intestine, stomach, kidney, bladder, uterus, ovary, and testes, as well as in lung, colon and prostate carcinomas. Immunogenic Brachyury polypeptides are disclosed herein. These polypeptides can be used in diagnostic assays for Brachyury expression, as well as for inducing an immune response to Brachyury. Polynucleotides encoding the immunogenic Brachyury polypeptides, vectors including these polypeptides, host cells transformed with these vectors, and methods of using these polypeptides, polynucleotides, vectors, and host cells are provided. Methods of diagnosing a Brachyury-expressing cancer are also provided. Exemplary cancers include lung, colon, small intestine, stomach, kidney, bladder, uterus, ovary, and testes and prostate cancers. Methods of treating cancer are also disclosed.

42 Claims, 6 Drawing Sheets

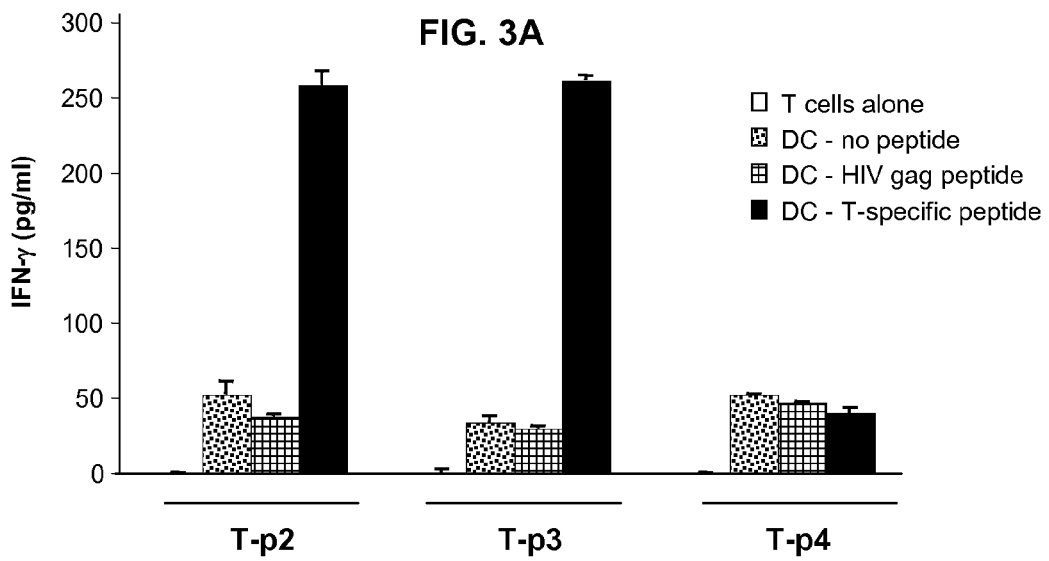
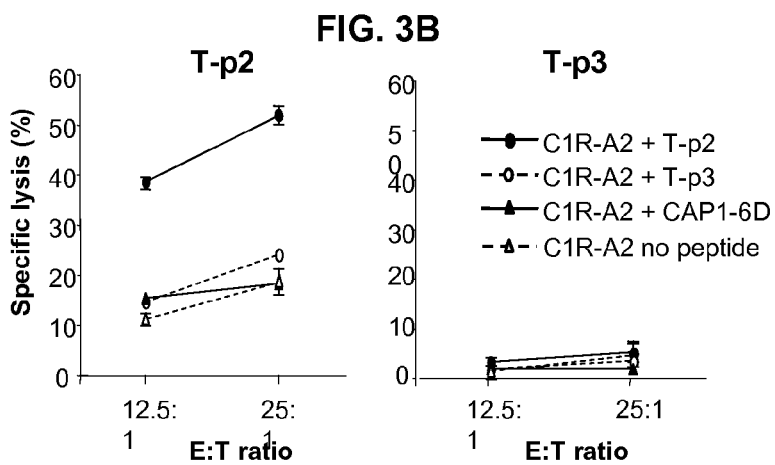
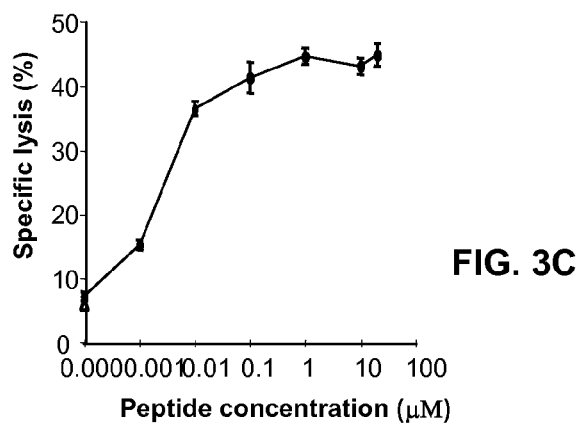

FIG. 5
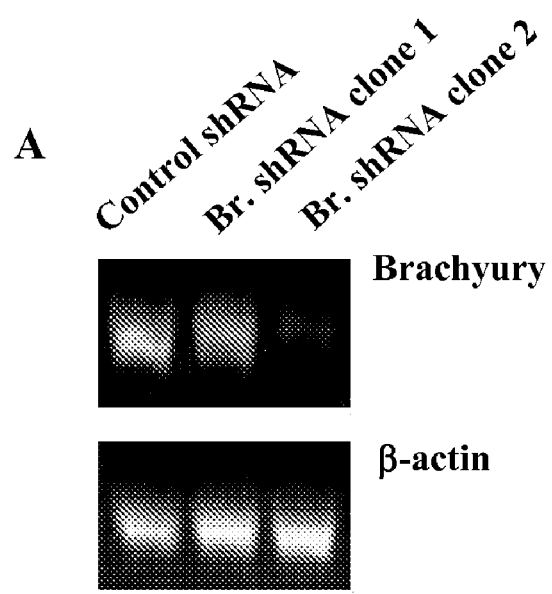
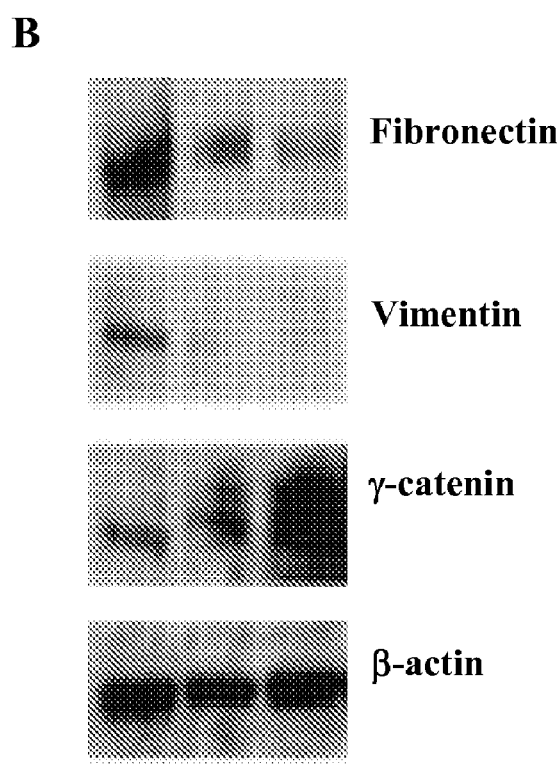

SEQUENCE LISTING

<160> NUMBER OF SEQ ID NOS: 22

<210> SEQ ID NO 1
<211> LENGTH: 435
<212> TYPE: PRT
<213> ORGANISM: Homo sapiens

<400> SEQUENCE: 1

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
```

```
                    85                  90                  95
Ala Asp Asn His Arg Trp Lys Tyr Val Asn Gly Glu Trp Val Pro Gly
                100                 105                 110

Gly Lys Pro Glu Pro Gln Ala Pro Ser Cys Val Tyr Ile His Pro Asp
            115                 120                 125

Ser Pro Asn Phe Gly Ala His Trp Met Lys Ala Pro Val Ser Phe Ser
        130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Leu Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Ser Gln Tyr Pro Ser Leu Trp Ser
            340                 345                 350

Val Ser Asn Gly Ala Val Thr Pro Gly Ser Gln Ala Ala Val Ser
        355                 360                 365

Asn Gly Leu Gly Ala Gln Phe Phe Arg Gly Ser Pro Ala His Tyr Thr
    370                 375                 380

Pro Leu Thr His Pro Val Ser Ala Pro Ser Ser Gly Ser Pro Leu
385                 390                 395                 400

Tyr Glu Gly Ala Ala Ala Thr Asp Ile Val Asp Ser Gln Tyr Asp
                405                 410                 415

Ala Ala Ala Gln Gly Arg Leu Ile Ala Ser Trp Thr Pro Val Ser Pro
            420                 425                 430

Pro Ser Met
        435

<210> SEQ ID NO 2
<211> LENGTH: 2518
<212> TYPE: DNA
<213> ORGANISM: Homo sapiens

<400> SEQUENCE: 2
tttgcttttg cttatttccg tccatttccc tctctgcgcg cggaccttcc ttttccagat    60
ggtgagagcc gcggggacac ccgacgccgg ggcaggctga tccacgatcc tgggtgtgcg   120
```

-continued

```
taacgccgcc tggggctccg tgggcgaggg acgtgtgggg acaggtgcac cggaaactgc    180
cagactggag agttgaggca tcggaggcgc gagaacagca ctactactgc ggcgagacga    240
gcgcggcgca tcccaaagcc cggccaaatg cgctcgtccc tgggagggga gggaggcgcg    300
cctggagcgg ggacagtctt ggtccgcgcc ctcctcccgg gtctgtgccg ggacccggga    360
cccgggagcc gtcgcaggtc tcggtccaag gggccccttt tctcggaagg cggcggcca     420 agagcaggga aggtggatct caggtagcga gtctgggctt cggggacggc ggggagggga    480
gccggacggg aggatgagct cccctggcac cgagagcgcg ggaaagagcc tgcagtaccg    540
agtggaccac ctgctgagcg ccgtggagaa tgagctgcag gcgggcagcg agaagggcga    600
ccccacagag cgcgaactgc gcgtgggcct ggaggagagc gagctgtggc tgcgcttcaa    660
ggagctcacc aatgagatga tcgtgaccaa gaacggcagg aggatgtttc cggtgctgaa    720
ggtgaacgtg tctggcctgg accccaacgc catgtactcc ttcctgctgg acttcgtggc    780
ggcggacaac caccgctgga agtacgtgaa cggggaatgg gtgccggggg caagccgga     840 gccgcaggcg cccagctgcg tctacatcca ccccgactcg cccaacttcg ggcccactg     900 gatgaaggct cccgtctcct tcagcaaagt caagctcacc aacaagctca cggaggggg     960 ccagatcatg ctgaactcct tgcataagta tgagcctcga atccacatag tgagagttgg    1020
gggtccacag cgcatgatca ccagccactg cttccctgag acccagttca tagcggtgac    1080
tgcttatcag aacgaggaga tcacagctct taaaattaag tacaatccat ttgcaaaagc    1140
tttccttgat gcaaaggaaa gaagtgatca caaagagatg atggaggaac ccggagacag    1200
ccagcaacct gggtactccc aatggggtg gcttcttcct ggaaccagca ccctgtgtcc    1260
acctgcaaat cctcatcctc agtttggagg tgccctctcc ctcccctcca cgcacagctg    1320
tgacaggtac ccaaccctga ggagccaccg gtcctcaccc taccccagcc ctatgctca    1380 tcggaacaat tctccaacct attctgacaa ctcacctgca tgtttatcca tgctgcaatc    1440
ccatgacaat tggtccagcc ttggaatgcc tgcccatccc agcatgctcc ccgtgagcca    1500
caatgccagc ccacctacca gctccagtca gtaccccagc ctgtggtctg tgagcaacgg    1560
cgccgtcacc ccgggctccc aggcagcagc cgtgtccaac gggctggggg cccagttctt    1620
ccggggctcc cccgcgcact acacacccct cacccatccg gtctcggcgc cctcttcctc    1680
gggatcccca ctgtacgaag gggcggccgc ggccacagac atcgtggaca gccagtacga    1740
cgccgcagcc caaggccgcc tcatagcctc atggacacct gtgtcgccac cttccatgtg    1800
aagcagcaag gccaggtcc cgaaagatgc agtgactttt tgtcgtggca gccagtggtg    1860
actggattga cctactaggt acccagtggc agtctcaggt taagaaggaa atgcagcctc    1920
agtaacttcc ttttcaaagc agtggaggag cacacggcac cttttcccag agccccagca    1980
tcccttgctc acacctgcag tagcggtgct gtcccaggtg gcttacagat gaacccaact    2040
gtggagatga tgcagttggc ccaacctcac tgacggtgaa aaaatgtttg ccagggtcca    2100 gaaactttt ttggtttatt tctcatacag tgtattggca actttggcac accagaattt    2160
gtaaactcca ccagtcctac tttagtgaga taaaaagcac actcttaatc ttcttccttg    2220
ttgctttcaa gtagttagag ttgagctgtt aaggacagaa taaaatcata gttgaggaca    2280
gcaggtttta gttgaattga aaatttgact gctctgcccc ctagaatgtg tgtattttaa    2340
gcatatgtag ctaatctctt gtgttgttaa actataactg tttcatattt ttcttttgac    2400
aaagtagcca aagacaatca gcagaaagca ttttctgcaa aataaacgca atatgcaaaa    2460
tgtgattcgt ccagttatta gtgaagcccc tccttttgtg agtatttact gtttattg      2518
```

```
<210> SEQ ID NO 3
<211> LENGTH: 9
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa can be Leu or Val

<400> SEQUENCE: 3

Trp Leu Leu Pro Gly Thr Ser Thr Xaa
1               5

<210> SEQ ID NO 4
<211> LENGTH: 20
<212> TYPE: DNA
<213> ORGANISM: Artificial sequence
<220> FEATURE:
<223> OTHER INFORMATION: Synthetic oligonucleotide primer

<400> SEQUENCE: 4
gggtggcttc ttcctggaac                                         20

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide primer

<400> SEQUENCE: 5
ttggagaatt gttccgatga g                                       21

<210> SEQ ID NO 6
<211> LENGTH: 26
<212> TYPE: DNA
<213> ORGANISM: Artificial sequence
<220> FEATURE:
<223> OTHER INFORMATION: Synthetic oligonucleotide primer

<400> SEQUENCE: 6
tgaaggtcgg agtcaacgga tttggt                                  26

<210> SEQ ID NO 7
<211> LENGTH: 24
<212> TYPE: DNA
<213> ORGANISM: Artificial sequence
<220> FEATURE:
<223> OTHER INFORMATION: Synthetic oligonucleotide primer

<400> SEQUENCE: 7
catgtgggcc atgaggtcca ccac                                    24

<210> SEQ ID NO 8
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 8
actggatgaa ggctcccgtc tcctt                                   25

<210> SEQ ID NO 9
<211> LENGTH: 25
<212> TYPE: DNA
<213> ORGANISM: Artificial sequence
```

```
<220> FEATURE:
<223> OTHER INFORMATION: Synthetic oligonucleotide primer

<400> SEQUENCE: 9
ccaaggctgg accaattgtc atggg                                              25

<210> SEQ ID NO 10
<211> LENGTH: 27
<212> TYPE: DNA
<213> ORGANISM: Artificial sequence
<220> FEATURE:
<223> OTHER INFORMATION: Synthetic oligonucleotide primer

<400> SEQUENCE: 10
atctggcacc acaccttcta caatgag                                            27

<210> SEQ ID NO 11
<211> LENGTH: 27
<212> TYPE: DNA
<213> ORGANISM: Artificial sequence
<220> FEATURE:
<223> OTHER INFORMATION: Synthetic oligonucleotide primer

<400> SEQUENCE: 11
cgtggtggtg aagctgtagc cgcgctc                                            27

<210> SEQ ID NO 12
<211> LENGTH: 9
<212> TYPE: PRT
<213> ORGANISM: Homo sapiens

<400> SEQUENCE: 12

Tyr Leu Ser Gly Ala Asp Leu Asn Leu
1               5

<210> SEQ ID NO 13
<211> LENGTH: 9
<212> TYPE: PRT
<213> ORGANISM: Homo sapiens

<400> SEQUENCE: 13

Ile Leu Lys Glu Pro Val His Gly Val
1               5

<210> SEQ ID NO 14
<211> LENGTH: 9
<212> TYPE: PRT
<213> ORGANISM: Homo sapiens

<400> SEQUENCE: 14

Ser Gln Tyr Pro Ser Leu Trp Ser Val
1               5

<210> SEQ ID NO 15
<211> LENGTH: 9
<212> TYPE: PRT
<213> ORGANISM: Homo sapiens

<400> SEQUENCE: 15

Trp Leu Leu Pro Gly Thr Ser Thr Leu
1               5

<210> SEQ ID NO 16
<211> LENGTH: 9
<212> TYPE: PRT
<213> ORGANISM: Homo sapiens
```

```
<400> SEQUENCE: 16

Arg Leu Ile Ala Ser Trp Thr Pro Val
1               5

<210> SEQ ID NO 17
<211> LENGTH: 10
<212> TYPE: PRT
<213> ORGANISM: Homo sapiens

<400> SEQUENCE: 17

Ala Met Tyr Ser Phe Leu Leu Asp Phe Val
1               5                   10

<210> SEQ ID NO 18
<211> LENGTH: 9
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be Leu or Val
<220> FEATURE:
<221> NAME/KEY: misc_feature
<222> LOCATION: (4)..(4)
<223> OTHER INFORMATION: Xaa can be Pro, Ser, Thr, Leu, or Val
<220> FEATURE:
<221> NAME/KEY: misc_feature
<222> LOCATION: (7)..(7)
<223> OTHER INFORMATION: Xaa can be Trp, Val, Leu, Ile, Ser, or thr
<220> FEATURE:
<221> NAME/KEY: misc_feature
<222> LOCATION: (9)..(9)
<223> OTHER INFORMATION: Xaa can be Leu or Val

<400> SEQUENCE: 18

Ser Xaa Tyr Xaa Ser Leu Xaa Ser Xaa
1               5

<210> SEQ ID NO 19
<211> LENGTH: 9
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be Ser, Thr, Ile, or Val
<220> FEATURE:
<221> NAME/KEY: misc_feature
<222> LOCATION: (9)..(9)
<223> OTHER INFORMATION: Xaa can be Leu or Val

<400> SEQUENCE: 19

Trp Leu Leu Xaa Gly Thr Ser Thr Xaa
1               5

<210> SEQ ID NO 20
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be Tyr or Trp
<220> FEATURE:
<221> NAME/KEY: misc_feature
<222> LOCATION: (6)..(6)
<223> OTHER INFORMATION: Xaa can be Trp and Thr

<400> SEQUENCE: 20

Xaa Leu Ile Ala Ser Thr Thr Pro Val
```

```
<210> SEQ ID NO 21
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be Arg, Tyr or Trp
<220> FEATURE:
<221> NAME/KEY: misc_feature
<222> LOCATION: (6)..(6)
<223> OTHER INFORMATION: Xaa can be Val, Lys, Ile, Ser or Thr

<400> SEQUENCE: 21

Xaa Leu Ile Ala Ser Xaa Thr Pro Val
1               5

<210> SEQ ID NO 22
<211> LENGTH: 10
<212> TYPE: PRT
<213> ORGANISM: Homo sapiens

<400> SEQUENCE: 22

Ala Leu Tyr Ser Phe Leu Leu Asp Phe Val
1               5                   10
```

BRACHYURY POLYPEPTIDES AND METHODS FOR USE

CROSS REFERENCE TO RELATED APPLICATIONS

This is the U.S. national stage of PCT Application No. PCT/US2008/055185, filed Feb. 27, 2008, which was published in English under PCT Article 21(2), which in turn claims the benefit of U.S. Provisional Application No. 60/904,236, filed Feb. 28, 2007, which is incorporated by reference.

FIELD

This application relates to the field of cancer therapeutics, specifically to molecules such as immunogenic peptides and inhibitory nucleic acids for the treatment of cancer.

BACKGROUND

Brachyury (also known as "T") was identified in mice as a dominant short tail mutant that is also a recessive lethal; homozygous T/T embryos die in mid-gestation due to a failure of posterior mesoderm formation (Chesley, J. Exp. Zool., 70: 429-459, 1935). The murine Brachyury gene has been cloned (Herrmann et al., Nature (Lond.), 343: 617-622, 1990), as well as the homologs in other species, such as humans. The expression of the human homologue of the mouse Brachyury was detected by RT-PCR in the notochord remnant, the nucleus pulposus, of human abortuses at 14-15 weeks gestation (Edwards et al., Genome Res., 6: 226-233, 1996).

Brachyury has generally proved a valuable marker for recognition of mesodermal differentiation (Herrmann et al., Trends Genet., 10: 280-286, 1994). For example, apart from expression in embryos themselves, Brachyury has been reported to be activated during the differentiation of certain murine EC and ES cell lines differentiating along mesodermal lineages in vitro (see, for example, Bain et al., Biochem. Biophys. Res. Commun., 223: 691-694, 1996). In humans, Brachyury has been shown to be expressed in teratocarcinomas (Gokhele et al., Cell Growth and Differentiation 11:157-62, 2000), chordomas (Vujovic et al., J. Pathol. 2: 157-65, 2006) and hemagioblastomas (Glasker et al., Cancer Res. 66: 4167-4172, 2006).

Immunotherapy involves evoking an immune response against cancer cells based on their production of target antigens. Immunotherapy based on cell-mediated immune responses involves generating a cell-mediated response to cells that produce particular antigenic determinants, while immunotherapy based on humoral immune responses involves generating specific antibodies to cells that produce particular antigenic determinants.

Recent studies show that immunotherapy of cancer patients may be dramatically improved by the finding that CD8+ CTLs recognize and kill tumor cells that display peptides from tumor-associated antigens within MHC Class I molecules. In clinical studies it has been found that effector CD8+ T cells play a major role in tumor regression. For example, several tumor antigens in prostate cancer models have been identified and HLA allele-specific peptides from those prostate cancer-associated antigens have been identified as CD8+ T cell epitopes. For example, HLA-A2.1 binding peptides were described that were derived from prostate specific antigen (PSA) (Correale et al., J Immunol 161:3186, 1998), prostate-specific membrane antigen (PSMA) (Tjoa et al., Prostate 28:65, 1996), prostate stem cell antigen (PSCA) (Kiessling et al., Int J Cancer 102:390, 2002), and prostate acid phosphatase (Peshwa et al., Prostate 36:129, 1998). For PSA, clinical trials are in progress using different vaccine strategies. However, there clearly is a need to identify additional antigens to aid in the diagnosis of cancers of different organs, and to produce peptides that can be used for immunotherapy of other types of cancer.

SUMMARY

It is disclosed herein that Brachyury is expressed in human tumors, specifically in tumors of the small intestine, stomach, kidney, bladder, uterus, ovary, and testes, as well as in lung, colon and prostate carcinomas. Immunogenic Brachyury polypeptides are disclosed herein. These Brachyury polypeptides can be used for inducing an immune response to Brachyury, as well as in diagnostic assays for Brachyury expression. In one example, the polypeptide is at most twelve consecutive amino acids in length, wherein the isolated polypeptide comprises the amino acid sequence set forth as WLLPGTSTX$_1$ (SEQ ID NO: 3), wherein X$_1$ is a leucine (L) or a valine (V).

Polynucleotides encoding the immunogenic Brachyury polypeptides, vectors including these polypeptides, host cells transformed with these vectors, and methods of using these polypeptides, polynucleotides, vectors, and host cells are provided herein. In one embodiment, a composition is disclosed that includes a first recombinant virus which has incorporated into a viral genome or infectable portion thereof a nucleic acid encoding the immunogenic Brachyury polypeptide and a second recombinant virus which has incorporated into a viral genome or infectable portion thereof one or more genes or DNA sequences encoding B7-1, B7-2, or B7-1 and B7-2, wherein the composition is able to coinfect a host cell resulting in co-expression of the polypeptide and the B7-1, B7-2, or B7-1 and B7-2 encoding genes or DNA sequences.

Methods of diagnosing a Brachyury-expressing cancer are also provided, that include the use of the disclosed immunogenic Brachyury polypeptides, nucleic acids encoding these polypeptides, or antibodies that specifically bind these polypeptides. Exemplary cancers include lung, colon, small intestine, stomach, kidney, bladder, uterus, ovary, and testes and prostate cancers.

Methods of inducing an immune response to Brachyury are also disclosed. The methods include the use of the immunogenic Brachyury polypeptides disclosed herein, nucleic acids encode these polypeptides, and/or viral vectors encoding an immunogenic Brachyury polypeptide, alone or in conjunction with other agents, such as B7-1, B7-2, and/or a cytokine and/or with traditional cancer therapies, such as surgery, radiation therapy and/or chemotherapy. Methods are disclosed for treating a subject having a tumor, such as, but not limited to, a small intestine, stomach, kidney bladder, uterus, ovary, testes, lung, colon or prostate tumor. Methods are also disclosed for treating a subject having a breast tumor, bronchial tube tumor, chronic lymphocytic leukemia (CLL) and other B cell-based malignancies. These methods include inducing an immune response to Brachyury and/or using an inhibitory nucleic acid, such as an siRNA or antisense molecule, to decrease Brachyury expression in order to treat the tumor.

The foregoing and other features and advantages will become more apparent from the following detailed description of several embodiments, which proceeds with reference to the accompanying figures.

BRIEF DESCRIPTION OF THE FIGURES

FIG. 1A is a digital image of RT-PCR results from human multiple tissues cDNA panels I and II. FIG. 1B is a digital image of RT-PCR results from various human blood fraction cDNAs. FIG. 1C is a digital image of results from RT-PCR of cDNA from tumor tissues (each tissue from an individual cancer patient) that were amplified for expression of Brachyury (upper panel) and GAPDH (bottom panel). Human DNA was used as a positive control for the PCR reaction; water was added to the tubes labeled as negative control.

FIG. 2A is a bar graph of results wherein peptides at 25 µM were analyzed for binding to T2 cells; a positive control (CAP 1-6D) and an HLA-A3 binding peptide (negative control) were used at the same concentration. MFI indicates mean fluorescence intensity. FIG. 2B is a line graph of results showing an analysis of half-life of peptide-MHC complexes that was conducted as described in Materials and Methods. For each peptide and the positive control CAP 1-6D, half-life time is given in minutes.

FIG. 3A-3C are graphs showing cytokine production and cytotoxic activity of CTLs specific for three Brachyury derived peptides. FIG. 3A is a bar graph showing results obtained when CD8+ T cells generated from PBMC of a healthy donor against peptides T-p2, T-p3, and T-p4 were stimulated for 24 hours in the presence of Brachyury (T)-specific peptides or irrelevant peptide-pulsed autologous DCs. IFN-γ was evaluated in the supernatants by ELISA. FIG. 3B is a line graph showing cytotoxic activity (6-hour assay) of CTLs generated with peptides T-p2 and T-p3 against peptide-pulsed C1R-A2 targets. Two effector-to-target ratios (E:T) were used as indicated. C1R-A2 cells were pulsed with 25 µM of T-p2 peptide (closed circles), T-p3 peptide (open circles), irrelevant CAP1-6D peptide (close triangles), and without peptide (open triangles). FIG. 3C is a line graph of results obtained when T2 cells were pulsed with various concentrations of T-p2 peptide as indicated and used as targets with T-p2 CTLs (at an effector-to-targets ratio equal to 12.5:1).

FIG. 4A is a line graph of results obtained when T-p2 CTLs from a normal donor were used as effectors against various tumor targets in an $^{111}$In 16-hour release assay, as indicated. FIG. 4B is a bar graph of results obtained when $^{111}$In-labeled H441 tumor cells were incubated with 25 µg/ml of a control IgG, anti-HLA-class I, or anti-HLA-class II MAb for 1 hour before the addition of T-p2 T cells. The E:T ratio was 20:1. FIG. 4C is a line graph of results obtained when CTLs established from the blood of a colorectal cancer patient (patient 1) and (FIG. 4D) an ovarian cancer patient (patient 2) were used after three IVS for cytotoxic killing of H441 and AsPC-1 tumor cells. FIG. 4E is a bar graph showing cytotoxic killing of LNCAP tumor cells by T-p2 T cells derived from patient 1. $^{111}$In-labeled LNCAP tumor cells were incubated with 25 µg/ml of a control IgG or an anti-HLA-A2,28 MAb for 1 hour before the addition of T-p2 T cells. FIG. 4F is a bar graph and a digital image of results obtained when T cells derived from patient 2 were used as effectors against various tumor targets, as indicated. Shown in the digital image is the expression of Brachyury and β-actin mRNA by RT-PCR in each tumor cell line.

FIGS. 5A-5B are digital images showing that stable knockdown of Brachyury expression induces a mesenchymal-to-epithelial transition in NCI-H460 lung carcinoma cancer cells. FIG. 5A is a digital image of an RT-PCR analysis of Brachyury and β-actin mRNA expression in NCI-H460 lung carcinoma cells stably transfected with a control shRNA or a Brachyury-specific shRNA construct (Br.shRNA clones 1 and 2). FIG. 5B is a digital image of the results obtained when the same cell lines were analyzed by western blot for expression of human fibronectin, vimentin, γ-catenin, and β-actin.

SEQUENCE LISTING

Figure 1A:
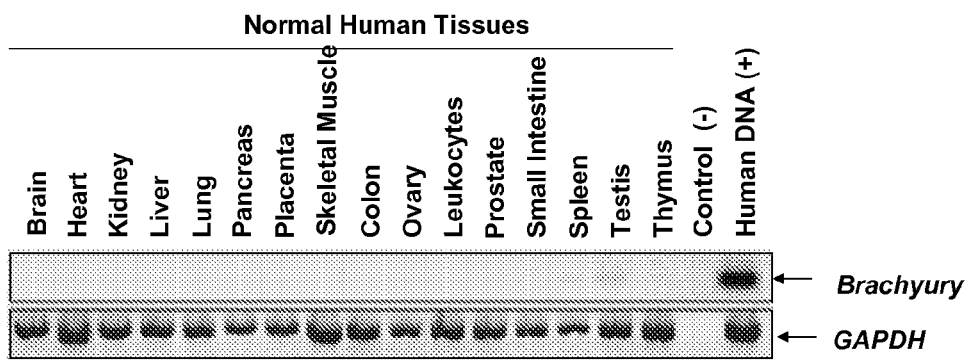
FIGS. 1A-1C are a set of digital images of RT-PCR analysis of Brachyury expression in human normal and tumor tissues.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file 899-82614-09 Sequence_Listing.txt, Nov. 4, 2011, 11.7 kilobytes], which is incorporated by reference herein. In the accompanying sequence listing:

SEQ ID NO: 1 is an exemplary amino acid sequence for a Brachyury protein.

SEQ ID NO: 2 is an exemplary nucleic acid sequence encoding a Brachyury polypeptide.

SEQ ID NO: 3 is the amino acid sequence of an immunogenic Brachyury polypeptide.

SEQ ID NOS: 4-11 are the nucleic acid sequences of primers.

SEQ ID NO: 12 is the amino acid sequence of a carcinoembryonic antigen (CEA) polypeptide.

SEQ ID NO: 13 is the amino acid sequence of a human immuno deficiency virus (HIV) polypeptide.

SEQ ID NOS: 14-22 are the amino acid sequence of exemplary Brachyury polypeptides.

DETAILED DESCRIPTION

It is disclosed herein that Brachyury is expressed in human tumors, specifically in tumors of the small intestine, stomach, kidney, bladder, uterus, ovary, and testes, as well as in lung, colon and prostate carcinomas. Brachyury is also expressed in chronic lymphocytic leukemia and other B cell malignancies. Immunogenic Brachyury polypeptides are disclosed herein. Nucleic acids encoding these polypeptides, vectors including these nucleic acids, and host cells transformed with the vectors are also disclosed. Methods for inducing an immune response to a tumor cell expressing Brachyury are also disclosed, as are methods for detecting a tumor that expresses Brachyury. Methods for treatment are also disclosed herein for the treatment of a tumor that expresses Brachyury, wherein the method includes administering an inhibitory nucleic acid.

Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided, along with particular examples:

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. Nos. 6,194,388; 6,207,646; 6,214,806; 6,218,371; 6,239,116; 6,339,068; 6,406,705; and 6,429,199). Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L and 41 BBL.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen, a uterine specific antigen, and/or a testes specific antigen. A tissue specific antigen may be expressed by more than one tissue, such as, but not limited to, an antigen that is expressed in more than one reproductive tissue, such as in both prostate and uterine tissue. A disease-specific antigen is expressed coincidentally with a disease process. Specific non-limiting examples of a disease-specific antigen are an antigen whose expression correlates with, or is predictive of, tumor formation, such as prostate cancer and/or uterine cancer and/or testicular cancer. A disease-specific antigen can be an antigen recognized by T cells or B cells.

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antibody: Immunoglobulin molecules and immunologically active portions of immunoglobulin molecules, i.e., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the VL and VH domains of a single arm of an antibody, (iv) a dAb fragment (Ward et al., Nature 341:544-546, 1989) which consists of a $V_H$ domain; (v) an isolated complementarity determining region (CDR); and (vi) a F(ab')$_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984). Humanized antibodies and fully human antibodies are also known in the art.

Animal: Living multi-cellular vertebrate organisms, a category that includes, for example, mammals and birds. The term mammal includes both human and non-human mammals. Similarly, the term "subject" includes both human and veterinary subjects.

Antisense, Sense, and Antigene: Double-stranded DNA (dsDNA) has two strands, a 5'->3' strand, referred to as the plus strand, and a 3'->5' strand (the reverse complement), referred to as the minus strand. Because RNA polymerase adds nucleic acids in a 5'->3' direction, the minus strand of the DNA serves as the template for the RNA during transcription.

Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Brachyury: The Brachyury gene is known to be important for the development of mesoderm during gastrulation. Brachyury is the founding member of a family of transcription factors, designated T-box transcription factors, characterized by a conserved DNA-binding domain (Papaioannou and Silver, Bioessays 20(1):9-19, 1998), that has an essential role in the formation and organization of mesoderm in vertebrates (see, for example, Kispert and Herrmann, Embo J 12(8):3211-20, 1993). For example, in *Xenopus*, Brachyury is an early-immediate response gene of mesoderm inducers, such as activin or TGF-β, and injection of Brachyury mRNA in embryos is sufficient to induce ectopic mesoderm development (Smith et al., Cell 67(1):79-87, 1991). In addition to the fundamental role of the T-box proteins in the control of developmental processes, several members of this family appear to be deregulated in cancer. The human Tbx2 gene has been reported to be amplified in pancreatic cancer cell lines (Mahlamakiet al., Genes Chromosomes Cancer 35(4):353-8, 2002) and over-expressed in BRCA-1- and BRCA-2-mutated breast tumors (Sinclair et al., Cancer Res 62(13):3587-9, 2002). Brachyury expression has been previously reported in human teratocarcinoma lines: a subset of germ cell tumors, teratocarcinomas are embryonal carcinoma cells with competence for mesoderm differentiation (Fan et al., Cancer Res 64(15):5132-9, 2004), as well as in chordomas (Vujovic et al, J Pathol 209(2): 157-65, 2006). Exemplary human brachyury amino acid and nucleic acid sequences are set forth in GENBANK® Accession No NP_003172 and GENBANK® Accession No. NM_003181, as available on Feb. 23, 2007, incorporated herein by reference Cancer or Tumor: A malignant neoplasm that has undergone characteristic anaplasia with loss of differentiation, increase rate of growth, invasion of surrounding tissue, and is capable of metastasis. For example, prostate cancer is a malignant neoplasm that arises in or from prostate tissue, ovarian cancer is a malignant neoplasm that arises in or from ovarian tissue, colon cancer is a malignant neoplasm that arises in or from colon tissue, and lung cancer is a malignant neoplasm that arises in the lungs. Residual cancer is cancer that remains in a subject after any form of treatment given to the subject to reduce or eradicate the cancer. Metastatic cancer is a cancer at one or more sites in the body other than the site of origin of the original (primary) cancer from which the metastatic cancer is derived. Cancer includes, but is not limited to, sarcomas and carcinomas. Prostate cancer is a malignant tumor, generally of glandular origin, of the prostate. Prostate cancers include adenocarcinomas and small cell carcinomas.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Conservative variants: "Conservative" amino acid substitutions are those substitutions that do not substantially affect or decrease an activity or antigenicity of an antigenic epitope of Brachyury. Specific, non-limiting examples of a conservative substitution include the following examples:

| Original Residue | Conservative Substitutions |
| --- | --- |
| Al | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity.

CD4: Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8: Cluster of differentiation factor 8, a T cell surface protein that mediates interaction with the MHC Class I molecule. Cells that express CD8 are often cytotoxic T cells.

Chemotherapy; chemotherapeutic agents: Any chemical agent with therapeutic usefulness in the treatment of diseases characterized by abnormal cell growth. Such diseases include tumors, neoplasms and cancer as well as diseases characterized by hyperplastic growth such as psoriasis. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., ©2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The immunogenic Brachyury polypeptides disclosed herein can be used in conjunction with additional chemotherapeutic agents.

Consists Essentially Of/Consists Of: With regard to a polypeptide, a polypeptide that consists essentially of a specified amino acid sequence if it does not include any additional amino acid residues. However, the polypeptide can include additional non-peptide components, such as labels (for example, fluorescent, radioactive, or solid particle labels), sugars or lipids. With regard to a polypeptide, a polypeptide that consists of a specified amino acid sequence does not include any additional amino acid residues, nor does it include additional non-peptide components, such as lipids, sugars or labels.

Costimulatory molecule: Although engagement of the TCR with peptide-MHC delivers one signal to the T cell, this signal alone can be insufficient to activate the T cell. Costimulatory molecules are molecules that, when bound to their ligand, deliver a second signal required for the T cell to become activated. The most well-known costimulatory molecule on the T cell is CD28, which binds to either B7-1 (also called CD80) or B7-2 (also known as CD86). An additional costimulatory molecule is B7-3. Accessory molecules that also provide a second signal for the activation of T cells include intracellular adhesion molecule (ICAM-1 and ICAM-2), leukocyte function associated antigen (LFA-1, LFA-2 and LFA-3). Integrins and tumor necrosis factor (TNF) superfamily members can also serve as co-stimulatory molecules.

Degenerate variant: A polynucleotide encoding an epitope of Brachyury that includes a sequence that is degenerate as a result of the genetic code. There are 20 natural amino acids, most of which are specified by more than one codon. Therefore, all degenerate nucleotide sequences are included in this disclosure as long as the amino acid sequence of the Brachyury polypeptide encoded by the nucleotide sequence is unchanged.

Dendritic cell (DC): Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells.

Diagnostic: Identifying the presence or nature of a pathologic condition, such as, but not limited to, a cancer, such as small intestine, stomach, kidney, bladder, uterus, ovary, testes, lung, colon or prostate cancer. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" means predicting the probability of development (for example, severity) of a pathologic condition, such as prostate cancer, or metastasis.

Epithelial-to-Mesenchymal Transition: The epithelium is the covering of internal and external surfaces of the body, including the lining of vessels and other small cavities that consists of cells joined by biological cementing substances. Generally, fully differentiated epithelial cells express proteins characteristic of a differentiated phenotype, such as insulin, and have a limited capacity to proliferate. The mesenchyme is the meshwork of loosely organized embryonic connective tissue in the mesoderm from which are formed the connective tissues of the body, along with the blood vessels and lymphatic vessels. Vimentin is one marker of mesenchymal cells. Mesenchymal cells generally have a greater capacity to proliferate in vitro than epithelial cells and are not fully differentiated. An "epithelial-to-mesenchymal" transition is a biological process wherein a cell, or a population of cells, from an epithelial phenotype convert to a less differentiated mesenchymal phenotype. A "mesenchymal-to-epithelial" transition is a biological process wherein a cell, or a population of cells, convert from a less differentiated mesenchymal phenotype to a more differentiated epithelial phenotype.

Epitope: An antigenic determinant. These are particular chemical groups or peptide sequences on a molecule that are antigenic (that elicit a specific immune response). An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like can be used. In one embodiment, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

Heterologous: Originating from separate genetic sources or species. A polypeptide that is heterologous to Brachyury originates from a nucleic acid that does not encode Brachyury. In one specific, non-limiting example, a polypeptide comprising nine consecutive amino acids from Brachyury, or at most 12 consecutive amino acids from Brachyury, and a heterologous amino acid sequence includes a β-galactosidase, a maltose binding protein, and albumin, hepatitis B surface antigen, or an immunoglobulin amino acid sequence. Generally, an antibody that specifically binds to a protein of interest will not specifically bind to a heterologous protein.

Host cells: Cells in which a vector can be propagated and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein (e.g. HLA-A02.01) and by their ability to stimulate CD4 and/or CD8 when presented in the context of the MHC protein. The characteristics of immunogenic polypeptides, are disclosed, for example, in PCT Publication No. WO 00/12706, which is incorporated herein by reference.

In one example, an immunogenic "Brachyury peptide" is a series of contiguous amino acid residues from the Brachyury protein generally between 7 and 20 amino acids in length, such as about 8 to 11 residues in length. Specific immunogenic Brachyury polypeptides are disclosed herein that are 9 or 10 amino acid residues in length, or at most 12 amino acids in length. Generally, immunogenic Brachyury polypeptide can be used to induce an immune response in a subject, such as a B cell response or a T cell response. In one example, an immunogenic Brachyury polypeptide, when bound to a Major Histocompatibility Complex Class I molecule, activates cytotoxic T lymphocytes (CTLs) against cells expressing wild-type Brachyury protein. Induction of CTLs using synthetic peptides and CTL cytotoxicity assays known in the art, see U.S. Pat. No. 5,662,907, which is incorporated herein by reference. In one example, an immunogenic peptide includes an allele-specific motif or other sequence such that the peptide will bind an MHC molecule and induce a cytotoxic T lymphocyte ("CTL") response against the antigen from which the immunogenic peptide is derived.

Immunogenic composition: A composition comprising an immunogenic Brachyury polypeptide or a nucleic acid encoding the immunogenic Brachyury polypeptide that induces a measurable CTL response against cells expressing Brachyury polypeptide, or induces a measurable B cell response (such as production of antibodies that specifically bind Brachyury) against a Brachyury polypeptide. For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and or immunogenic polypeptide, in pharmaceutically acceptable carriers, and/or other agents. An immunogenic composition can optionally include an adjuvant, a costimulatory molecule, or a nucleic acid encoding a costimulatory molecule. A Brachyury polypeptide, or nucleic acid encoding the polypeptide, can be readily tested for its ability to induce a CTL by art-recognized assays.

Inhibiting or treating a disease: Inhibiting a disease, such as tumor growth, refers to inhibiting the full development of a disease. In several examples, inhibiting a disease refers to lessening symptoms of a tumor, such as preventing the development of paraneoplastic syndrome in a person who is known to have a cancer, or lessening a sign or symptom of the tumor or reducing tumor volume. "Treatment" refers to a therapeutic intervention that ameliorates a sign or symptom of a disease or pathological condition related to the disease, such as the tumor.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Linker sequence: A linker sequence is an amino acid sequence that covalently links two polypeptide domains. Linker sequences can be included in the between the Brachyury epitopes disclosed herein to provide rotational freedom to the linked polypeptide domains and thereby to promote proper domain folding and presentation to the MHC. By way of example, in a recombinant polypeptide comprising two Brachyury domains, linker sequences can be provided between them, such as a polypeptide comprising Brachyury polypeptide-linker-Brachyury polypeptide. Linker sequences, which are generally between 2 and 25 amino acids in length, are well known in the art and include, but are not limited to, the glycine(4)-serine spacer (GGGGS×3) described by Chaudhary et al., *Nature* 339:394-397, 1989.

Lymphocytes: A type of white blood cell that is involved in the immune defenses of the body. There are two main types of lymphocytes: B cells and T cells.

Major Histocompatibility Complex (MHC): A generic designation meant to encompass the histocompatability antigen systems described in different species, including the human leukocyte antigens ("HLA").

Mammal: This term includes both human and non-human mammals. Similarly, the term "subject" includes both human and veterinary subjects.

Neoplasm: An abnormal cellular proliferation, which includes benign and malignant tumors, as well as other proliferative disorders.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence, such as a sequence that encodes a Brachyury polypeptide. Generally, operably linked DNA sequences are contiguous and, where necessary to join two protein-coding regions, in the same reading frame.

Peptide Modifications: Brachyury epitopes include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an immunogenic Brachyury polypeptide having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition or a cell to achieve a desired effect in a subject being treated. For instance, this can be the amount necessary to induce an immune response, inhibit tumor growth, reduce tumor volume or to measurably alter outward symptoms of the tumor. When administered to a subject, a dosage will generally be used that will achieve target tissue concentrations (for example, in lymphocytes) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (e.g., glycosylation or phosphorylation). In one embodiment, the polypeptide is a Brachyury polypeptide. A polypeptide can be between 3 and 30 amino acids in length. In one embodiment, a polypeptide is from about 7 to about 25 amino acids in length. In yet another embodiment, a polypeptide is from about 8 to about 12 amino acids in length. In yet another embodiment, a peptide is about 9 amino acids in length. With regard to polypeptides, the word "about" indicates integer amounts. Thus, in one example, a polypeptide "about" 9 amino acids in length is from 8 to 10 amino acids in length.

Probes and primers: A probe comprises an isolated nucleic acid attached to a detectable label or reporter molecule. Primers are short nucleic acids, preferably DNA oligonucleotides, of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example by polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers can be selected that comprise about 20, 25, 30, 35, 40, 50 or more consecutive nucleotides.

Purified: The epitopes of Brachyury disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982). Substantial purification denotes purification from other proteins or cellular components. A substantially purified protein is at least about 60%, 70%, 80%, 90%, 95%, 98% or 99% pure. Thus, in one specific, non-limiting example, a substantially purified protein is 90% free of other proteins or cellular components.

Thus, the term purified does not require absolute purity; rather, it is intended as a relative term. For example, a purified nucleic acid is one in which the nucleic acid is more enriched than the nucleic acid in its natural environment within a cell. In additional embodiments, a nucleic acid or cell preparation is purified such that the nucleic acid or cell represents at least about 60% (such as, but not limited to, 70%, 80%, 90%, 95%, 98% or 99%) of the total nucleic acid or cell content of the preparation, respectively.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (for example, GC v. AT content), and nucleic acid type (for example, RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual,* 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a Brachyury polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a Brachyury polypeptide are typically characterized by possession of at least 75%, for example at least 80%, sequence identity counted over the full length alignment with the amino acid sequence of Brachyury using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and can possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Small interfering RNAs: Synthetic or naturally-produced small double stranded RNAs (dsRNAs) that can induce gene-specific inhibition of expression in invertebrate and vertebrate species are provided. These RNAs are suitable for interference or inhibition of expression of a target gene and comprise double stranded RNAs of about 15 to about 40 nucleotides containing a 3' and/or 5' overhang on each strand having a length of O— to about 5-nucleotides, wherein the sequence of the double stranded RNAs is essentially identical to a portion of a coding region of the target gene for which interference or inhibition of expression is desired. The double stranded RNAs can be formed from complementary ssRNAs or from a single stranded RNA that forms a hairpin or from expression from a DNA vector.

Specific binding agent: An agent that binds substantially only to a defined target. Thus a Brachyury specific binding agent is an agent that binds substantially to a Brachyury polypeptide. In one embodiment, the specific binding agent is a monoclonal or polyclonal antibody that specifically binds Brachyury.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8 T cell is a cytotoxic T lymphocyte. In another embodiment, a CD8 cell is a suppressor T cell.

Therapeutically active polypeptide: An agent, such as an epitope of Brachyury that causes induction of an immune response, as measured by clinical response (for example increase in a population of immune cells, increased cytolytic activity against cells that express Brachyury, or measurable reduction of tumor burden). Therapeutically active molecules can also be made from nucleic acids. Examples of a nucleic acid based therapeutically active molecule is a nucleic acid sequence that encodes a Brachyury epitope, wherein the nucleic acid sequence is operably linked to a control element such as a promoter. Another example of a therapeutically active molecule is an antisense molecule or a siRNA for Brachyury.

In one embodiment, a therapeutically effective amount of a composition, such as a Brachyury polypeptide, is an amount used to generate an immune response, or to treat cancer in a subject. In several examples, "treatment" refers to a therapeutic intervention that ameliorates a sign or symptom of a cancer, or a reduction in tumor burden.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors. Vectors also include vectors for expression in yeast cells.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Immunogenic Brachyury Peptides

Brachyury (also known as "T-protein") is a polypeptide which is transcribed in the mesoderm. In one embodiment, the polypeptide has a sequence set forth as:

```
                                         (SEQ ID NO: 1)
MSSPGTESAGKSLQYRVDHLLSAVENELQAGSEKGDPTERELRVGLEESE

LWLRFKELTNEMIVTKNGRRMFPVLKVNVSGLDPNAMYSFLLDFVAADNH

RWKYVNGEWVPGGKPEPQAPSCVYIHPDSPNFGAHWMKAPVSFSKVKLTN

KLNGGGQIMLNSLHKYEPRIHIVRVGGPQRMITSHCFPETQFIAVTAYQN

EEITALKIKYNPFAKAFLDAKERSDHKEMMEEPGDSQQPGYSQWGWLLPG

TSTLCPPANPHPQFGGALSLPSTHSCDRYPTLRSHRSSPYPSPYAHRNNS

PTYSDNSPACLSMLQSHDNWSSLGMPAHPSMLPVSHNASPPTSSSQYPSL

WSVSNGAVTPGSQAAAVSNGLGAQFFRGSPAHYTPLTHPVSAPSSSGSPL

YEGAAAATDIVDSQYDAAAQGRLIASWTPVSPPSM
(see also GENBANK® Accession No NP_003172 and
GENBANK® Accession No. NM_003181, as available on
Feb. 23, 2007, incorporated herein by reference).
```

In other embodiments, Brachyury has an amino acid sequence at least 90% identical to SEQ ID NO: 1, for example a polypeptide that has at least about 91%, 92%, 93%, 94%, 95%, 96%, 97%, 98% or 99% sequence identity to SEQ ID NO: 1.

Using the genetic code, one of skill in the art can readily produce a nucleic acid sequence encoding Brachyury. In one example, Brachyury is encoded by a nucleic acid having a sequence set forth as:

(SEQ ID NO: 2)
```
tttgcttttg cttatttccg tccatttccc tctctgcgcg
cggaccttcc ttttccagat ggtgagagcc gcggggacac
ccgacgccgg ggcaggctga tccacgatcc tgggtgtgcg
taacgccgcc tggggctccg tgggcgaggg acgtgtgggg
acaggtgcac cggaaactgc cagactggag agttgaggca
tcggaggcgc gagaacagca ctactactgc ggcgagacga
gcgcggcgca tcccaaagcc cggccaaatg cgctcgtccc
tgggagggga gggaggcgcg cctggacgcg ggacagtctt
ggtccgcgcc ctcctcccgg gtctgtgccg ggacccggga
cccgggagcc gtcgcaggtc tcggtccaag gggccccttt
tctcggaagg gcggcggcca agagcaggga aggtggatct
caggtagcga gtctgggctt cgggacggg ggagggga
gccggacggg aggatgagct cccctggcac cgagagcgcg
ggaaagagcc tgcagtaccg agtggaccac ctgctgagcg
ccgtggagaa tgagctgcag gcgggcagcg agaagggcga
ccccacagag cgcgaactgc gcgtgggcct ggaggagagc
gagctgtggc tgcgcttcaa ggagctcacc aatgagatga
tcgtgaccaa gaacggcagg aggatgtttc cggtgctgaa
ggtgaacgtg tctggcctgg accccaacgc catgtactcc
ttcctgctgg acttcgtggc ggcggacaac caccgctgga
agtacgtgaa cggggaatgg gtgccggggg gcaagccgga
gccgcaggcg cccagctgcg tctacatcca ccccgactcg
cccaacttcg gggcccactg gatgaaggct cccgtctcct
tcagcaaagt caagctcacc aacaagctca acggaggggg
ccagatcatg ctgaactcct tgcataagta tgagcctcga
atccacatag tgagagttgg gggtccacag cgcatgatca
ccagccactg cttccctgag acccagttca tagcggtgac
tgcttatcag aacgaggaga tcacagctct taaaattaag
tacaatccat ttgcaaaagc tttccttgat gcaaaggaaa
gaagtgatca caaagagatg atggaggaac ccggagacag
ccagcaacct gggtactccc aatggggggtg gcttcttcct
ggaaccagca ccctgtgtcc acctgcaaat cctcatcctc
agtttggagg tgccctctcc ctcccctcca cgcacagctg
tgacaggtac ccaaccctga ggagccaccg gtcctcaccc
tacccagcc cctatgctca tcggaacaat tctccaacct
attctgacaa ctcacctgca tgtttatcca tgctgcaatc
ccatgacaat tggtccagcc ttggaatgcc tgcccatccc
agcatgctcc ccgtgagcca caatgccagc ccacctacca
gctccagtca gtacccagc ctgtggtctg tgagcaacgg
cgccgtcacc ccgggctccc aggcagcagc cgtgtccaac
gggctggggg cccagttctt ccggggctcc cccgcgcact
acacacccct cacccatccg gtctcggcgc cctcttcctc
gggatcccca ctgtacgaag gggcggccgc ggccacagac
atcgtggaca gccagtacga cgccgcagcc caaggccgcc
tcatagcctc atggacacct gtgtcgccac cttccatgtg
aagcagcaag gcccaggtcc cgaaagatgc agtgacttt
tgtcgtggca gccagtggtg actggattga cctactaggt
acccagtggc agtctcaggt taagaaggaa atgcagcctc
agtaacttcc ttttcaaagc agtggaggag cacacggcac
cttccccag agccccagca tcccttgctc acacctgcag
tagcggtgct gtcccaggtg gcttacagat gaacccaact
gtggagatga tgcagttggc ccaacctcac tgacggtgaa
aaaatgtttg ccagggtcca gaaactttt ttggtttatt
tctcatacag tgtattggca actttggcac accagaattt
gtaaactcca ccagtcctac tttagtgaga taaaaagcac
actcttaatc ttcttccttg ttgctttcaa gtagttagag
ttgagctgtt aaggacagaa taaaatcata gttgaggaca
gcaggtttta gttgaattga aaatttgact gctctgcccc
ctagaatgtg tgtattttaa gcatatgtag ctaatctctt
gtgttgttaa actataactg tttcatattt ttcttttgac
aaagtagcca aagacaatca gcagaaagca ttttctgcaa
aataaacgca atatgcaaaa tgtgattcgt ccagttatta
gtgaagcccc tccttttgtg agtatttact gtttattg
```

Immunogenic fragments of Brachyury (and Brachyury itself), can be chemically synthesized by standard methods. If desired, polypeptides can also be chemically synthesized by emerging technologies. One such process is described in W. Lu et al., *Federation of European Biochemical Societies Letters*. 429:31-35, 1998. Polypeptides can also be produced using molecular genetic techniques, such as by inserting a nucleic acid encoding Brachyury or an epitope thereof into an expression vector, introducing the expression vector into a host cell, and isolating the polypeptide (see below).

Brachyury polypeptides are disclosed herein that can be used to induce an immune response (are immunogenic). These peptides comprise at most twelve amino acids, such as eleven, ten amino acids, or nine consecutive amino acids of a Brachyury polypeptide.

An isolated polypeptide is disclosed that includes at most twelve consecutive amino acids from Brachyury, wherein the isolated polypeptide comprises the amino acid sequence set forth as WLLPGTSTX$_1$ (SEQ ID NO: 3), wherein X$_1$ is a leucine (L) or a valine (V). In some embodiments, amino acid 1 (X$_1$) is a leucine. In additional embodiments, amino acid 1 (X$_1$) is a valine. In one example the polypeptide consists essentially of the amino acid sequence set forth as SEQ ID NO: 3. Thus, in one example, the polypeptide consists essentially of SEQ ID NO: 3, wherein amino acid X$_1$ is a valine (V), and in another example the polypeptide consists essentially of SEQ ID NO: 3, wherein amino acid X$_1$ is a leucine. In additional examples, the polypeptide is eleven amino acids in length or ten amino acids in length. In further examples, the isolated polypeptide consists of the amino acid sequence set forth as SEQ ID NO: 3.

In additional embodiments the isolated Brachyury polypeptide is nine to twelve amino acids in length and comprises the amino acid sequence set forth as SQYPSLWSV (SEQ ID NO: 14), WLLPGTSTL (SEQ ID NO: 15), RLIASWTPV (SEQ ID NO: 16), or AMYSFLLDFV (SEQ ID NO: 17). In several examples, the isolated Brachyury polypeptide is nine or ten amino acids in length, and comprises one of the amino acid sequences set forth as SEQ ID NOs: 14-17. In additional examples, the isolated Brachyury polypeptide consists of the amino acid sequence set forth as one of SEQ ID NO: 14-17.

In additional embodiments, the Brachyury polypeptide is nine to twelve amino acids in length, and comprises the amino acid sequence: $SX_2YX_3SLX_4SX_5$ (SEQ ID NO: 18), wherein $X_2$ and $X_5$ are either a valine or a leucine, wherein $X_3$ is proline (P), serine (S), threonine (T), leucine (L), or valine (V) and wherein $X_4$ is tryptophan (W), valine (V), leucine (L), isoleucine (I), serine (S) or threorine (T). In further examples, the Brachyury polypeptide is nine, ten or eleven amino acids in length, and comprises the amino acid sequence set forth as SEQ ID NO: 18, wherein $X_5$ is one of valine or a leucine. In additional examples, the Brachyury polypeptide consists of the amino acid sequence set forth as SEQ ID NO: 18 wherein $X_5$ is a valine or a leucine. The following exemplary Brachyury polypeptides are encompassed by the present disclosure:

T-p1a: SLYPSLWSV
(SEQ ID NO: 18, wherein $X_2$ is L, $X_3$ is P, $X_4$ is W and $X_5$ is V)

T-p1b: SLYPSLWSL
(SEQ ID NO: 18, wherein $X_2$ is L, $X_3$ is P, $X_4$ is W and $X_5$ is L)

T-p1c: $SX_2YSSLWSV$
(SEQ ID NO: 18, wherein $X_2$ is Q or L, $X_3$ is Y, $X_4$ is W and $X_5$ is V)

T-p1d: $SX_2YTSLWSV$
(SEQ ID NO: 18, wherein $X_2$ is Q or L, $X_3$ is T, $X_4$ is W, and $X_5$ is V)

T-p1e: $SX_2YLSLWSV$
(SEQ ID NO: 18, wherein $X_2$ is Q or L, $X_3$ is L, $X_4$ is W and $X_5$ is V)

T-p1f: $SX_2YVSLWSV$
(SEQ ID NO: 18, wherein $X_2$ is Q or L, $X_3$ isV, $X_4$ is W and $X_5$ is V)

T-p1g: $SX_2YPSLVSV$
(SEQ ID NO: 18, wherein $X_2$ is Q or L, $X_3$ is P, $X_4$ is V and $X_5$ is V)

T-p1h: $SX_2YPSLLSV$
(SEQ ID NO: 18, wherein $X_2$ is Q or L, $X_3$ is P, $X_4$ is L and $X_5$ is V)

T-p1i: $SX_2YPSLISV$
(SEQ ID NO: 18, wherein $X_2$ is Q or L, $X_3$ is P, $X_4$ is I and $X_5$ is V)

T-p1j: $SX_2YPSLSSV$
(SEQ ID NO: 18, wherein $X_2$ is Q or L, $X_3$ is P, $X_4$ is S and $X_5$ is V)

T-p1k: $SX_2YPSLTSV$
(SEQ ID NO: 18, wherein $X_2$ is Q or L, $X_3$ is P, $X_4$ is T and $X_5$ is V)

In further embodiments, the Brachyury polypeptide is nine to twelve amino acids in length, and comprises the amino acid sequence: $WLLX_6GTSTX_7$ (SEQ ID NO: 19), wherein $X_6$ is serine (S), threonine (T), isoleucine (I), valine (V) and wherein $X_7$ is leucine (L) or valine. In further examples, the Brachyury polypeptide is nine or ten amino acids in length, and comprises the amino acid sequence set forth as SEQ ID NO: 19, wherein $X_7$ is one of valine or a leucine. In additional examples, the Brachyury polypeptide consists of the amino acid sequence set forth as SEQ ID NO: 19 wherein $X_{5-7}$ is a valine or a leucine. The following exemplary polypeptides are encompassed by this disclosure:

Tp2b: $WLLSGTSTX_7$
(SEQ ID NO: 19, wherein $X_6$ is S, and $X_7$ is L or V)

Tp2c: $WLLTGTSTX_7$
(SEQ ID NO: 19, wherein $X_6$ is T, and $X_7$ is L or V)

Tp2d: $WLLIGTSTX_7$
(SEQ ID NO: 19, wherein $X_6$ is I, and $X_7$ is L or V)

Tp2e: $WLLVGTSTX_7$
(SEQ ID NO: 19, wherein $X_6$ is V, and $X_7$ is L or V)

In additional embodiments, the Brachyury polypeptide is nine to twelve amino acids in length, and comprises the amino acid sequence $X_8LIASX_{11}TPV$ (SEQ ID NO: 20), wherein $X_8$ is tyrosine (Y) or tryptophan (W) and $X_{11}$ is threonine (T) or tryptophan (W). The Brachyury polypeptide can be nine or ten amino acids in length, and comprises the amino acid sequence set forth as $X_8LIASTTPV$ (SEQ ID NO: 20, wherein $X_8$ is one of tyrosine (Y) or tryptophan (W). In additional examples, the Brachyury polypeptide consists of the amino acid sequence set forth as SEQ ID NO: 20 wherein $X_8$ is a tryptophan or a tyrosine. Thus, the following polypeptides are encompassed by the present disclosure:

T-p3a: YLIASWTPV (SEQ ID NO: 20, wherein $X_8$ is Y)

T-p3b: WLIASWTPV (SEQ ID NO: 20, wherein $X_8$ is W)

In another set of embodiments, the isolated Brachyury polypeptide is nine to twelve amino acids in length, and comprises the amino acid sequence: $X_9LIASX_{10}TPV$ (SEQ ID NO: 21), wherein $X_9$ is an arginine (R), tyrosine (Y) or tryptophan (W) and $X_{10}$ is a valine (V), lysine (L), isoleucine (I), serine (S) or threonine (T). In some examples, the isolated Brachyury polypeptide is nine or ten amino acids in length, and comprises the amino acid sequence set forth as $X_9LIASTTPV$ (SEQ ID NO: 21, $X_9$ is an arginine, tyrosine or tryptophan and $X_{10}$ is a valine, lysine, isoleucine, serine or threonine). In additional examples, the Brachyury polypeptide consists of the amino acid sequence set forth as SEQ ID NO: 21 wherein $X_9$ is an arginine, tyrosine or tryptophan and $X_{10}$ is a valine, serine, isoleucine, or threonine. Thus, the following polypeptides are encompassed by the present disclosure:

Tp3c: $X_9$ LIASVTPV
(SEQ ID NO: 21, wherein $X_9$ = R, Y, or W And $X_{10}$ is V)

Tp3d: $X_9$ LIASLTPV
(SEQ ID NO: 21, wherein $X_9$ = R, Y, or W And $X_{10}$ is V)

-continued

Tp3e: X₉ LIASITPV
(SEQ ID NO: 21, wherein X₉ = R, Y, or W And X₁₀ is V)

Tp3f: X₉ LIASSTPV
(SEQ ID NO: 21, wherein X₉ = R, Y, or W And X₁₀ is V)

Tp3g: X₉ LIASTTPV
(SEQ ID NO: 21, wherein X₉ = R, Y, or W And X₁₀ is V)

In an additional embodiment, the isolated Brachyury polypeptide is ten to twelve amino acids in length, and comprises the amino acid sequence ALYSFLLDFV (SEQ ID NO: 22, T-p4a). In some examples, the isolated Brachyury polypeptide is ten or eleven amino acids in length and comprises ALYSFLLDFV (SEQ ID NO: 22). In an additional example, the isolated Brachyury polypeptide consists of ALYSFLLDFV (SEQ ID NO: 22).

In several embodiments, the isolated Brachyury polypeptide is include in a fusion protein. Thus, the fusion protein can include the Brachyury polypeptide (see above) and a second heterologous moiety, such as a myc protein, an enzyme or a carrier (such as a hepatitis carrier protein or bovine serum albumin) covalently linked to the Brachyury polypeptide. In additional embodiments, the protein consists of the Brachyury polypeptide. Thus, a second heterologous moiety is non-covalently linked to the Brachyury polypeptide. For example, the polypeptide can be nine or ten acid amino acids in length, and consists of the sequence set forth as one of SEQ ID NO: 3, SEQ ID NO: 14, SEQ ID NO: 15, SEQ ID NO: 16, SEQ ID NO: 17, SEQ ID NO: 18, SEQ ID NO: 19, SEQ ID NO:20, SEQ ID NO:21, SEQ ID NO: 22.

These above-described brachyury polypeptides are immunogenic, and thus can be used to induce an immune response in a subject. The Brachyury polypeptides disclosed herein do not include all the additional consecutive amino acids of SEQ ID NO:1. In one embodiment, the polypeptide does not include amino acids 1-15 of SEQ ID NO: 1.

Without being bound by theory, it is believed that the presentation of peptides by MHC Class I molecules involves binding to the cleft in an MHC Class I molecule through the anchor residues of the peptide and ultimate presentation on the cell surface. Depending upon the particular anchor residues, among other things, certain peptides can bind more tightly to particular HLA molecules than others. Peptides that bind well are usually "dominant" epitopes, while those that bind less well are often "subdominant" or "cryptic" epitopes. Dominant epitopes of either self proteins or foreign proteins evoke strong tolerance or immune responses. Subdominant or cryptic epitopes generate weak responses or no responses at all. Without being bound by theory, tighter binding by dominant epitopes to HLA molecules results in their denser presentation on the cell surface, greater opportunity to react with immune cells and greater likelihood of eliciting an immune response or tolerance. MHC Class I molecules present epitopes from endogenous proteins for presentation to CTL cells. HLA A, HLA B and HLA C molecules bind peptides of about eight to ten amino acids in length (such as nine amino acids in length) that have particular anchoring residues. The anchoring residues recognized by an HLA Class I molecule depend upon the particular allelic form of the HLA molecule. A CD8+ T cell bears T cell receptors that recognize a specific epitope when presented by a particular HLA molecule on a cell. When a CTL precursor that has been stimulated by an antigen presenting cell to become a cytotoxic T lymphocyte contacts a cell that bears such an HLA-peptide complex, the CTL forms a conjugate with the cell and destroys it. In several examples presented herein, the polypeptides that are disclosed bind and are presented by HLA-A2.1.

In several examples, the Brachyury polypeptide can be repeated in series, such that the polypeptide includes several copies of the immunogenic Brachyury polypeptide. However, only one copy of the Brachyury polypeptide can be included in an immunogenic molecule. In several examples, two, three, four, five copies of the Brachyury polypeptide are included in an immunogenic molecule. The copies of the Brachyury polypeptide can be separated by peptide linkers.

In additional examples, the polypeptide can be a fusion protein and can also include heterologous sequences to Brachyury (such as amino acid sequences of at least nine amino acids in length that are not included in SEQ ID NO: 1). Thus, in several specific non-limiting examples, the immunogenic peptide is a fusion polypeptide, for example the polypeptide includes six sequential histidine residues, a β-galactosidase amino acid sequence, or an immunoglobulin amino acid sequence. The polypeptide can also be covalently linked to a carrier. Suitable carriers include, but are not limited to, a hepatitis B small envelope protein HBsAg. This protein has the capacity to self assemble into aggregates and can form viral-like particles. The preparation of HBsAg is well documented, see for example European Patent Application Publication No. EP-A-0 226 846, European Patent Application Publication No. EP-A-0 299 108 and PCT Publication No. WO 01/117554, and the amino acid sequence disclosed, for example, in Tiollais et al., Nature, 317: 489, 1985, and European Patent Publication No. EP-A-0 278 940, and PCT Publication No. WO 91/14703, all of which are incorporated herein by reference.

As noted above, the fusion polypeptide can optionally include repetitions of one or more of the Brachyury polypeptides disclosed herein. In one specific, non-limiting example, the polypeptide includes two, three, four, five, or up to ten repetitions of one of a Brachyury polypeptide. A linker sequence can optionally be included between the Brachyury polypeptides. In all of these examples, the polypeptide does not include the full-length Brachyury amino acid sequence, such as the amino acid sequence set forth as SEQ ID NO: 1.

The Brachyury polypeptides disclosed herein can be chemically synthesized by standard methods, or can be produced recombinantly. An exemplary process for polypeptide production is described in Lu et al., *Federation of European Biochemical Societies Letters.* 429:31-35, 1998. They can also be isolated by methods including preparative chromatography and immunological separations.

A Brachyury polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

Polynucleotides encoding the Brachyury polypeptides disclosed herein are also provided. These polynucleotides include DNA, cDNA and RNA sequences which encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

A nucleic acid encoding a Brachyury polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding a Brachyury polypeptide include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides of the invention can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, may inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on K lactis are known, such as pKLAC1. Thus, in one example, after amplification in bacteria, plasmids can be introduced into the corresponding yeast auxotrophs by methods similar to bacterial transformation.

The brachyury peptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the brachyury polypeptides disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell. Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell. Biol., 5:431-437; Sorge et al., 1984, Mol. Cell. Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding a Brachyury polypeptide is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses useful in practicing the present invention include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

In some cases, vaccinia viral vectors may elicit a strong antibody response. Thus, while numerous boosts with vaccinia vectors are possible, its repeated use may not be useful in certain instances. However, this sensitivity problem can be minimized by using pox from different genera for boosts. In one example, when the first or initial pox virus vector is vaccinia, the second and subsequent pox virus vectors are selected from the pox viruses from a different genus such as suipox, avipox, capripox or an orthopox immunogenically distinct from vaccinia.

The vaccinia virus genome is known in the art. It is composed of a HIND F13L region, TK region, and an HA region. Recombinant vaccinia virus has been used to incorporate an exogenous gene for expression of the exogenous gene product (see, for example, Perkus et al. *Science* 229:981-984, 1985; Kaufman et al. *Int. J. Cancer* 48:900-907, 1991; Moss *Science* 252:1662, 1991). A gene encoding an antigen of interest, such as an immunogenic Brachyury polypeptide, can be incorporated into the HIND F13L region or alternatively incorporated into the TK region of recombinant vaccinia virus vector (or other nonessential regions of the vaccinia virus genome). Baxby and Paoletti (*Vaccine* 10:8-9, 1992) disclose the construction and use as a vector, of the non-replicating poxvirus, including canarypox virus, fowlpox virus and other avian species. Sutter and Moss (*Proc. Nat'l. Acad. Sci. U.S.A.* 89:10847-10851, 1992) and Sutter et al. (*Virology* 1994) disclose the construction and use as a vector, the non-replicating recombinant Ankara virus (MVA, modified vaccinia Ankara) in the construction and use of a vector.

Suitable vectors are disclosed, for example, in U.S. Pat. No. 6,998,252, which is incorporated herein by reference. In one example, a recombinant poxvirus, such as a recombinant vaccinia virus is synthetically modified by insertion of a chimeric gene containing vaccinia regulatory sequences or DNA sequences functionally equivalent thereto flanking DNA sequences which in nature are not contiguous with the flanking vaccinia regulatory DNA sequences that encode a Brachyury polypeptide. The recombinant virus containing such a chimeric gene is effective at expressing the Brachyury polypeptide. In one example, the vaccine viral vector comprises (A) a segment comprised of (i) a first DNA sequence encoding a Brachyury polypeptide and (ii) a poxvirus promoter, wherein the poxvirus promoter is adjacent to and exerts transcriptional control over the DNA sequence encoding a Brachyury polypeptide; and, flanking said segment, (B) DNA from a nonessential region of a poxvirus genome. The viral vector can encode a selectable marker. In one example, the poxvirus includes, for example, a thymidine kinase gene (see U.S. Pat. No. 6,998,252, which is incorporated herein by reference).

Poxyiral vectors that encode a Brachyury polypeptide include at least one expression control element operationally linked to the nucleic acid sequence encoding the Brachyury polypeptide. The expression control elements are inserted in the poxyiral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the Brachyury polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding the Brachyury polypeptide, are known in the art. Such techniques involve, for example, homologous recombination between the viral DNA sequences flanking the DNA sequence in a donor plasmid and homologous sequences present in the parental virus (Mackett et al., 1982, Proc. Natl. Acad. Sci. USA 79:7415-7419). In particular, recombinant viral vectors such as a poxyiral vector can be used in delivering the gene. The vector can be constructed for example by steps known in the art, such as steps analogous to the methods for creating synthetic recombinants of the fowlpox virus described in U.S. Pat. No. 5,093,258, incorporated herein by reference. Other techniques include using a unique restriction endonuclease site that is naturally present or artificially inserted in the parental viral vector to insert the heterologous DNA.

Generally, a DNA donor vector contains the following elements: (i) a prokaryotic origin of replication, so that the vector may be amplified in a prokaryotic host; (ii) a gene encoding a marker which allows selection of prokaryotic host cells that contain the vector (e.g., a gene encoding antibiotic resistance); (iii) at least one DNA sequence encoding the Brachyury polypeptide located adjacent to a transcriptional promoter capable of directing the expression of the sequence; and (iv) DNA sequences homologous to the region of the parent virus genome where the foreign gene(s) will be inserted, flanking the construct of element (iii). Methods for constructing donor plasmids for the introduction of multiple foreign genes into pox virus are described in WO91/19803, incorporated herein by reference.

Generally, DNA fragments for construction of the donor vector, including fragments containing transcriptional promoters and fragments containing sequences homologous to the region of the parent virus genome into which foreign DNA sequences are to be inserted, can be obtained from genomic DNA or cloned DNA fragments. The donor plasmids can be mono, di-, or multivalent (i.e., can contain one or more inserted foreign DNA sequences). The donor vector can contain an additional gene that encodes a marker that will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., 1988, J. Virol. 62:1046; Falkner and Moss, 1988, J. Virol. 62:1849; Franke et al., 1985, Mol. Cell. Biol. 5:1918), as well as genes such as the *E. coli* lacZ gene, that permit identification of recombinant viral plaques by calorimetric assay (Panicali et al., 1986, Gene 47:193-199).

The DNA gene sequence to be inserted into the virus can be placed into a donor plasmid, such as an *E. coli* or a *Salmonella* plasmid construct, into which DNA homologous to a section of DNA such as that of the insertion site of the poxvirus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA that is the desired insertion region. With a parental pox viral vector, a pox promoter is used. The resulting plasmid construct is then amplified by growth within *E. coli* bacteria and isolated. Next, the isolated plasmid containing the DNA gene sequence to be inserted is transfected into a cell culture, for example chick embryo fibroblasts, along with the parental virus, for example poxvirus. Recombination between homologous pox DNA in the plasmid and the viral genome respectively results in a recombinant poxvirus modified by the presence of the promoter-gene construct in its genome, at a site that does not affect virus viability.

As noted above, the DNA sequence is inserted into a region (insertion region) in the virus that does not affect virus viability of the resultant recombinant virus. One of skill in the art can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. The TK gene has been found in all pox virus genomes examined, including leporipoxvirus (Upton et al., 1986, J. Virology 60:920); shope fibromavirus; capripoxvirus (Gershon et al., 1989, J. Gen. Virol. 70:525) Kenya sheep-1; orthopoxvirus (Weir et al., 1983, J. Virol. 46:530) vaccinia (Esposito et al., 1984, Virology 135:561); monkeypox and variola virus (Hruby et al., 1983, PNAS 80:3411) vaccinia (Kilpatrick et al., 1985, Virology 143:399); Yaba monkey tumor virus; avipoxvirus (Binns et al., 1988, J. Gen. Virol. 69:1275); fowlpox; (Boyle et al., 1987, Virology 156:355); fowlpox (Schnitzlein et al., 1988, J. Virological Methods 20:341); fowlpox, quailpox; entomopox (Lytvyn et al., 1992, J. Gen. Virol. 73:3235-3240). In vaccinia, in addition to the TK region, other insertion regions include, for example, the HindIII M fragment. In fowlpox, in addition to the TK region, other insertion regions include, for example, the BamHI J fragment (Jenkins et al., 1991, AIDS Research and Human Retroviruses 7:991-998) the ECORI-HindIII fragment, EcoRV-HindIII fragment, BamHI fragment and the HindIII fragment set forth in EPO Application No. 0 308220 A1 (see also Calvert et al., 1993, J. Virol. 67:3069-3076; Taylor et al., 1988, Vaccine 6:497-503; Spehner et al., 1990; Boursnell et al., 1990, J. Gen. Virol. 71:621-628).

In swinepox, insertion sites include the thymidine kinase gene region. In addition to the requirement that the gene be inserted into an insertion region, successful expression of the inserted gene by the modified poxvirus requires the presence of a promoter operably linked to the desired gene. Generally, the promoter is placed so that it is located upstream from the gene to be expressed. Promoters are well known in the art and can readily be selected depending on the host and the cell type you wish to target. In one example, in poxviruses, pox viral promoters are used, such as the vaccinia 7.5K, 40K or fowlpox promoters such as FPV C1A. Enhancer elements can also be used in combination to increase the level of expression. Furthermore, inducible promoters can be utilized.

Homologous recombination between donor plasmid DNA and viral DNA in an infected cell can result in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (see U.S. Pat. No. 4,603,112 and PCT Publication No. WO 89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK- and can be selected on this basis (Mackett et al., 1982, Proc. Natl. Acad. Sci. USA 79:7415). Alternatively, co-integration of a gene encoding a marker or indicator gene with the foreign gene(s) of interest, as described above, can be used to identify recombinant progeny. One specific non-limiting example of an indicator gene is the *E. coli* lacZ gene. Recombinant viruses expressing beta-galactosidase can be selected using a chromogenic substrate for the enzyme (Panicali et al., 1986, Gene 47:193). Once a recombinant virus has been identified, a variety of well-known methods can be used to assay the expression of the Brachyury sequence encoded by the inserted DNA fragment. These methods include black plaque assay (an in situ enzyme immunoassay performed on viral plaques), Western blot analysis, radioimmunoprecipitation (RIPA), and enzyme immunoassay (EIA).

This disclosure encompasses a recombinant virus comprising more than one antigen of interest for the purpose of having a multivalent vaccine. For example, the recombinant virus may comprise the virus genome or portions thereof, the nucleic acid sequence encoding the Brachyury polypeptide and a nucleic acid sequence encoding a hepatitis B surface antigen.

In one embodiment, a composition is provided that includes a recombinant virus comprising a vaccinia virus genome or portions thereof, the nucleic acid sequence encoding a Brachyury polypeptide and a recombinant virus comprising the nucleic acid sequence encoding the immunostimulatory molecule, B 7.1 alone or in combination with the nucleic acid sequence encoding the immunostimulatory molecule, B7-2, or a recombinant virus containing both the genes for a tumor antigen and an immunostimulatory molecule. This disclosure also encompasses a recombinant virus comprising the Brachyury polypeptide that is administered with a second recombinant virus comprising the virus genome or portion thereof, and one or more nucleic acid sequences encoding one or more B7 molecules, such as a recombinant vaccinia virus expressing B7-1 and/or B7-2. It is disclosed in U.S. Pat. No. 893,869 (incorporated by reference herein) that the rapid infection of tumor cells with these recombinant viruses demonstrates that vaccinia can authentically express these proteins and that they are functional molecules. Following transfer of the nucleic acids, weakly immunogenic syngeneic tumors expressing these recombinant molecules are rejected by immunocompetent hosts.

Thus, in one example, recombinant virus is disclosed that is a recombinant vaccinia virus containing B7-1 and a recombinant vaccinia virus containing B7-2 (designated rV-B7-1 and rV-B7-2, respectively); the composition can include rV-B7-1 and/or rV-B7-2 in combination with an immunogenic Brachyury polypeptide.

The B7 molecule includes but is not limited to B7-1, B7-2 and analogs thereof. The B7 gene may be cloned from mammalian sources, including but not limited to mammalian tissues, genomic libraries or cDNA libraries, such as from murine or human sources. Without being bound by theory, co-stimulatory molecules of the B7 family (namely B7-1, B7-2, and possibly B7.3) are believed to be members of the immunoglobulin gene superfamily. These molecules are present on macrophages, dendritic cells, monocytes (antigen presenting cells (APCs)). Significant amplification of the immune response against a given antigen generally does not occur without co-stimulation (June et al. (*Immunology Today* 15:321-331, 1994); Chen et al. (*Immunology Today* 14:483-486); Townsend et al. (*Science* 259:368-370)). Freeman et al. (*J. Immunol.* 143:2714-2722, 1989) report cloning and sequencing of B7-1 gene. Azuma et al. Nature 366:76-79, 1993) report cloning and sequencing B7-2 gene. Thus, in one embodiment the B7-1 gene or the B7-2 genes are administered in conjunction with the Brachyury polypeptide. The insertion of nucleic acids encoding B7-1 and B7-2 into vaccinia virus has been disclosed (see for example, U.S. Pat. No. 6,893,869, incorporated herein by reference; this U.S. patent also discloses the use of a nucleic acid encoding IL-2 in a vaccinia virus). Several vectors including IL-2, B7-1 and B7-2 have been deposited with the American Type Culture Collection (ATCC) on Oct. 3, 1994 under the terms of the Budapest Treaty (for example, rV-CEA/$_n$IL-2 (ATCC Designation VR 2480), rV-$_m$B7-2 (ATCC Designation VR 2482); and rV-$_m$B7-1 (ATCC Designation VR 2483)).

DNA sequences encoding a Brachyury polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding a Brachyury polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods Methods in Enzymology 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding a Brachyury polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Therapeutic Methods and Pharmaceutical Compositions

The Brachyury polypeptides disclosed herein, or nucleic acids encoding the Brachyury polypeptides, can be used to generate an immune response in a subject. In several examples, the subject has a tumor that expresses Brachyury. Thus, in several embodiments, the methods include administering to a subject with cancer a therapeutically effective amount of one or more of the Brachyury polypeptides disclosed herein, in order to generate an immune response.

The methods can include selecting a subject in need of treatment, such as a subject with a tumor that expresses Brachyury. In several examples, the methods include selecting a subject with a tumor of the small intestine, stomach, kidney, bladder, uterus, ovaries, testes lung, colon or prostate. In additional examples, the method includes selecting a subject with a tumor of B cell origin, such as chronic lymphocytic leukemia (CLL), a B cell lymphoma, Burkitt's lymphoma or a Hodgkin's lymphoma.

In exemplary applications, compositions are administered to a subject having a disease, such as cancer (for example, small intestine, stomach, kidney, bladder, uterus, ovary, testes, lung colon, or prostate cancer), in an amount sufficient to raise an immune response to Brachyury-expressing cells. Administration induces a sufficient immune response to slow the proliferation of such cells or to inhibit their growth, or to reduce a sign or a symptom of the tumor. Amounts effective for this use will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer.

A Brachyury polypeptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular, subcutaneous, intraperitoneal or intravenous injection, but even oral, nasal, transdermal or anal administration is contemplated. In one embodiment, administration is by subcutaneous or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

In one specific, non-limiting example, the Brachyury polypeptide is administered in a manner to direct the immune response to a cellular response (that is, a cytotoxic T lymphocyte (CTL) response), rather than a humoral (antibody) response.

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J. Sci. Am. 6(Suppl 1):S61-6; Cao et al., 1998, Stem Cells 16(Suppl 1):251-60; Kuiper et al., 2000, Adv. Exp. Med. Biol. 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1 B7-2, OX-40L, 41 BBL and ICAM-1 are administered.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

In yet another embodiment, to induce a CTL response to an immunogenic Brachyury polypeptide, a MHC Class II-restricted T-helper epitope is added to the immunogenic Brachyury polypeptide to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," in Powell et al., eds., *Vaccine Design, the Subunit and Adjuvant Approach*, Plenum Press, New York, 1995).

A pharmaceutical composition including a Brachyury polypeptide is thus provided. These compositions are use to generate an immune response, such as for immunotherapy. In one embodiment, the Brachyury polypeptide is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol.* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif, or a biological adjuvant (see above).

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems, Technomic Publishing Co., Inc., Lancaster, Pa.,* 1993). Numerous additional systems for controlled delivery of therapeutic proteins are known (e.g., U.S. Pat. No. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In another embodiment, a pharmaceutical composition includes a nucleic acid encoding an Brachyury polypeptide. A therapeutically effective amount of the Brachyury polynucleotide can be administered to a subject in order to generate an immune response. In one specific, non-limiting example, a therapeutically effective amount of the Brachyury polynucleotide is administered to a subject to treat prostate cancer or breast cancer.

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J. Sci. Am. 6(Suppl 1):S61-6; Cao et al., 1998, Stem Cells 16(Suppl 1):251-60; Kuiper et al., 2000, Adv. Exp. Med. Biol. 465:381-90). These molecules can be administered systemically to the host. It should be noted that these molecules can be co-administered via insertion of a nucleic acid encoding the molecules into a vector, for example, a recombinant pox vector (see, for example, U.S. Pat. No. 6,045,802). In various embodiments, the nucleic acid encoding the biological adjuvant can be cloned into same vector as the Brachyury polypeptide coding sequence, or the nucleic acid can be cloned into one or more separate vectors for co-administration. In addition, nonspecific immuno-modulating factors such as Bacillus Cahnette-Guerin (BCG) and levamisole can be co-administered.

One approach to administration of nucleic acids is direct immunization with plasmid DNA, such as with a mammalian expression plasmid. As described above, the nucleotide sequence encoding a Brachyury polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In another approach to using nucleic acids for immunization, a Brachyury polypeptide can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

A first recombinant virus, such as a poxvirus (for example, vaccine virus) encoding a Brachyury immunogenic polypeptide can be used in conjunction with a second recombinant virus which has incorporated into a viral genome or infectable portion thereof one or more genes or DNA sequences encoding B7-1, B7-2, or B7-1 and B7-2, wherein the composition is able to coinfect a host cell resulting in coexpression of the polypeptide and the B7-1, B7-2, or B7-1 and B7-2 encoding genes or DNA sequences (see U.S. Pat. Nos. 6,893,869, and 6,045,908, which are incorporated by reference herein). The expression of the B7 gene family has been shown to be an important mechanism of anti-tumor responses in both mice and humans.

When a viral vector is utilized, it is desirable to provide the recipient with a dosage of each recombinant virus in the composition in the range of from about $10^5$ to about $10^{10}$ plaque forming units/mg mammal, although a lower or higher dose can be administered. The composition of recombinant viral vectors can be introduced into a mammal either prior to any evidence of a cancer, or to mediate regression of the disease in a mammal afflicted with the cancer. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the cancerous lesion in a pharmaceutically acceptable carrier.

Generally, the quantity of recombinant viral vector, carrying the nucleic acid sequence of one or more Brachyury polypeptides to be administered is based on the titer of virus particles. An exemplary range of the immunogen to be administered is $10^5$ to $10^{10}$ virus particles per mammal, such as a human.

In the embodiment where a combination of a first recombinant viral vector carrying a nucleic acid sequence of one or more Brachyury polypeptides and a second recombinant viral vector carrying the nucleic acid sequence of one or more immunostimulatory molecules is used, the mammal can be immunized with different ratios of the first and second recombinant viral vector. In one embodiment the ratio of the first vector to the second vector is about 1:1, or about 1:3, or about 1:5. Optimal ratios of the first vector to the second vector may easily be titered using the methods known in the art (see, for example, U.S. Pat. No. 6,893,869, incorporated herein by reference).

In one embodiment the recombinant viruses have been constructed to express cytokines (such as TNF-α, IL-6, GM-CSF, and IL-2), and co-stimulatory and accessory molecules (B7-1, B7-2) alone and in a variety of combinations. Simultaneous production of an immunostimulatory molecule and the Brachyury polypeptide enhances the generation of specific effectors. Without being bound by theory, dependent upon the specific immunostimulatory molecules, different mechanisms might be responsible for the enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. For example, IL-2, IL-6, interferon, tumor necrosis factor, or a nucleic acid encoding these molecules, can be administered in conjunction with a Brachyury immunogenic polypeptide, or a nucleic acid encoding a Brachyury polypeptide. The co-expression of a Brachyury polypeptide together with at least one immunostimulatory molecule can be effective in an animal model to show anti-tumor effects.

In one embodiment, a nucleic acid encoding a Brachyury polypeptide is introduced directly into cells. For example, the nucleic acid can be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 µg/kg to about 50 mg/kg, and typically are about 0.005 mg/kg to about 5 mg/kg (see, for example, U.S. Pat. No. 5,589,466).

In one specific, non-limiting example, a pharmaceutical composition for intravenous administration would include about 0.1 µg to 10 mg of immunogenic Brachyury polypeptide per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In another method, antigen presenting cells (APCs), such as dendritic cells, are pulsed or co-incubated with peptides comprising a Brachyury polypeptide in vitro. In one specific, non-limiting example, the antigen presenting cells can be autologous cells. A therapeutically effective amount of the antigen presenting cells can then be administered to a subject.

The Brachyury polypeptide can be delivered to the dendritic cells or to dendritic cell precursors via any method known in the art, including, but not limited to, pulsing dendritic cells directly with antigen, or utilizing a broad variety of antigen delivery vehicles, such as, for example, liposomes, or other vectors known to deliver antigen to cells. In one specific, non-limiting example an antigenic formulation includes about 0.1 µg to about 1,000 µg, or about 1 to about 100 µg of a selected Brachyury polypeptide. The Brachyury polypeptide can also be administered with agents that promote dendritic cell maturation. Specific, non-limiting examples of agents of use are interleukin-4 (IL-4) and granulocyte/macrophage colony stimulating factor (GM-CSF), or flt-3 ligand (flt-3L). The preparation can also contain buffers, excipients, and preservatives, amongst other ingredients.

In one embodiment, mature antigen presenting cells are generated to present the immunogenic Brachyury polypeptide. These dendritic cells are then administered alone (or in combination with another agent) to a subject with a tumor that expresses Brachyury, such as a small intestine, stomach, kidney, bladder, uterus, ovary, testis, lung colon and/or prostate cancer. The dendritic cells can also be administered to a subject with a tumor of B cell origin, such as chronic lymphocytic leukemia (CLL), a B cell lymphoma, Burkitt's lymphoma or a Hodgkin's lymphoma.

In another embodiment, the mature dendritic cells are administered in conjunction with a chemotherapeutic agent.

Alternatively, the APCs are used to sensitize CD8 cells, such as tumor infiltrating lymphocytes (TILs) from tumors or peripheral blood lymphocytes (PBLs). The TILs or PBLs can be from the same subject (autologous) that is to be treated. Alternatively, the TILs or PBLs can be heterologous. However, they should at least be MHC Class-I restricted to the HLA types the subject possesses. An effective amount of the sensitized cells are then administered to the subject.

Peripheral blood mononuclear cells (PBMCs) can be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived, such as Brachyury (for example, SEQ ID NO: 1).

The cells can be administered to a subject to inhibit the growth of cells of Brachyury expressing tumors. In these applications, a therapeutically effective amount of activated antigen presenting cells, or activated lymphocytes, are administered to a subject suffering from a disease, in an amount sufficient to raise an immune response to Brachyury-expressing cells. The resulting immune response is sufficient to slow the proliferation of such cells or to inhibit their growth, or to reduce a sign or a symptom of the tumor.

In a supplemental method, any of these immunotherapies is augmented by administering a cytokine, such as interleukin (IL)-2, IL-3, IL-6, IL-10, IL-12, IL-15, GM-CSF, or interferons.

In a further method, any of these immunotherapies is augmented by administering an additional chemotherapeutic agent. In one example, this administration is sequential. Examples of such agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testosterone proprionate and fluoxymesterone). Examples of the most commonly used chemotherapy drugs that can be concurrently administered with the disclosed immunotherapy include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Methods of Treatment Using Specific Binding Agents

Expression of Brachyury is associated with tumor cell migration and invasion. Brachyury is expressed in small intestine, stomach, kidney, bladder, uterus, ovaries, testes lung, colon and prostate tumors but not in most normal tissues. In addition, expression of Brachyury is associated with epithelial-to mesenchymal transition. Moreover, Brachyury is expressed in tumors of B cell origin, such as chronic lymphocytic leukemia (CLL), Epstein-Barr virus transformed B cells, Burkitt's and Hodgkin's lymphomas. Reagents that can reduce the expression of Brachyury also can be used to treat tumors that express Brachyury. The reagents can be used alone, or can be used in combination with the immunogenic Brachyury polypeptides disclosed herein.

The methods can include selecting a subject in need of treatment, such as a subject with a tumor that expresses Brachyury. In several examples, the methods include selecting a subject with a tumor of the small intestine, stomach, kidney, bladder, uterus, ovaries, testes lung, colon or prostate. In additional examples, the method includes selecting a subject with a tumor of B cell origin, such as chronic lymphocytic leukemia (CLL), a B cell lymphoma, Burkitt's lymphoma or a Hodgkin's lymphoma.

In one example, the method includes administering a therapeutically effective amount of a specific binding agent that preferentially binds to Brachyury. The specific binding agent can be an inhibitor such as a siRNA or an antisense molecule that specifically binds Brachyury mRNA (such as an mRNA encoding SEQ ID NO: 1). Inhibition of Brachyury does not require 100% inhibition, but can include at least a reduction if not a complete inhibition of cell growth or differentiation associated with a specific pathological condition. Treatment of a tumor by reducing Brachyury expression can include delaying the development of the tumor in a subject (such as preventing metastasis of a tumor) by altering the ability of the tumor to metastasize. Treatment of a tumor also includes reducing signs or symptoms associated with the presence of such a tumor (for example by reducing the size or volume of the tumor or a metastasis thereof) by decreasing the number of metastases. In some examples decrease or slowing metastasis of the tumor, or reducing the size or volume of the tumor, is an alteration of at least 10%, at least 20%, at least 50%, or at least 75. In some examples, treatment using the methods disclosed herein prolongs the time of survival of the subject. Treatment can also result in a down-regulation of mesenchymal markers (such as fibronectin, vimentin and/or N-cadherin) and an up-regulation of epithelial markers (such as E-cadherin or g-catenin).

Specific binding agents are agents that bind with higher affinity to Brachyury, than to other molecules. For example, a specific binding agent can be one that binds with high affinity to Brachyury but does not substantially bind to another gene or gene product. For example, the specific binding agent interferes with gene expression (transcription, processing, translation, post-translational modification), such as, by interfering with Brachyury mRNA and blocking translation into protein.

A reduction of Brachyury protein expression in a target cell may be obtained by introducing into cells an antisense or other suppressive construct based on the Brachyury coding sequence. For antisense suppression, a nucleotide sequence from a Brachyury encoding sequence, e.g. all or a portion of the Brachyury cDNA or gene, is arranged in reverse orientation relative to the promoter sequence in the transformation vector.

The introduced sequence need not be the full length Brachyury gene, and need not be exactly homologous to the equivalent sequence found in the cell type to be transformed. Thus, portions or fragments of a nucleic acid encoding Brachyury (SEQ ID NO: 2) could also be used to knock out or suppress expression. Generally, however, where the introduced sequence is of shorter length, a higher degree of identity to the native Brachyury sequence will be needed for effective antisense suppression. The introduced antisense sequence in the vector may be at least 15 nucleotides in length, and improved antisense suppression typically will be observed as the length of the antisense sequence increases.

The length of the antisense sequence in the vector advantageously may be greater than 100 nucleotides, and can be up to about the full length of the Brachyury cDNA or gene. For suppression of the Brachyury gene itself, transcription of an antisense construct results in the production of RNA molecules that are the reverse complement of mRNA molecules transcribed from the endogenous Brachyury gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA. Expression of Brachyury can also be reduced using small inhibitory RNAs, for instance using techniques similar to those described previously (see, e.g., Tuschl et al., *Genes Dev* 13, 3191-3197, 1999; Caplen et al., *Proc. Nat'l Acad. Sci. U.S.A.* 98, 9742-9747, 2001; and Elbashir et al., *Nature* 411, 494-498, 2001). Methods of making siRNA that can be used clinically are known in the art. Exemplary siRNAs are commercially available from several sources, such as Sigma Aldrich and Dharmacon, and therapeutic siRNAs can readily be produced using methods known in the art.

Suppression of endogenous Brachyury expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

In certain examples, expression vectors are employed to express the inhibitor nucleic acid, such as the antisense, ribozyme or siRNA molecule (see above for additional information on vectors and expression systems). For example, an expression vector can include a nucleic acid sequence encoding the antisense, ribozyme or siRNA molecule. In a particular example, the vector contains a sequence(s) encoding both strands of a siRNA molecule comprising a duplex. In another example, the vector also contains sequence(s) encoding a single nucleic acid molecule that is self-complementary and thus forms a siRNA molecule. Non-limiting examples of such expression vectors are described in Paul et al., *Nature Biotechnology* 19:505, 2002; Miyagishi and Taira, *Nature Biotechnology* 19:497, 2002; Lee et al., *Nature Biotechnology* 19:500, 2002; and Novina et al., *Nature Medicine*, online publication Jun. 3, 2003, and additional vectors are described above.

In other examples, inhibitory nucleic acids, such as siRNA molecules include a delivery vehicle, including inter alia liposomes, for administration to a subject, carriers and diluents and their salts, and can be present in pharmaceutical compositions. Nucleic acid molecules can be administered to cells by a variety of methods known to those of skill in the art, including, but not restricted to, encapsulation in liposomes, by iontophoresis, or by incorporation into other delivery vehicles, such as hydrogels, cyclodextrins, biodegradable nanocapsules, and bioadhesive microspheres, or by proteinaceous vectors (see, for example, O'Hare and Normand, International PCT Publication No. WO 00/53722, see also the additional methods described above).

Alternatively, the nucleic acid/vehicle combination can be locally delivered such as into a tumor by direct injection or by use of an infusion pump. Direct injection of the nucleic acid molecules of the disclosure, whether subcutaneous, intramuscular, or intradermal, can take place using standard needle and syringe methodologies, or by needle-free technologies such as those described by Barry et al., International PCT Publication No. WO 99/31262. Other delivery routes include, but are not limited to, oral delivery (such as in tablet or pill form), intrathecal or intraperitoneal delivery (see below). For example, intraperitoneal delivery can take place by injecting the treatment into the peritoneal cavity of the subject in order to directly deliver the molecules to the tumor site. More detailed descriptions of nucleic acid delivery and administration are provided in Sullivan et al., PCT WO 94/02595, Draper et al., PCT Publication No. WO93/23569, Beigelman et al., PCT WO99/05094, and Klimuk et al., PCT Publication No. WO 99/04819, all of which are incorporated by reference herein.

Alternatively, certain siRNA molecules can be expressed within cells from eukaryotic promoters. Those skilled in the art will recognize that any nucleic acid can be expressed in eukaryotic cells using the appropriate DNA/RNA vector (see above). The activity of such nucleic acids can be augmented by their release from the primary transcript by an enzymatic nucleic acid (Draper et al., PCT Publication No. WO 93/23569, and Sullivan et al., PCT Publication No. WO 94/02595).

In other examples, siRNA molecules can be expressed from transcription units (see for example, Couture et al., 1996, TIG 12:510) inserted into DNA or RNA vectors. The recombinant vectors can be DNA plasmids or viral vectors. siRNA expressing viral vectors can be constructed based on, for example, but not limited to, adeno-associated virus, retrovirus, adenovirus, lentivirus or alphavirus. In another example, pol III based constructs are used to express nucleic acid molecules of the invention (see for example, Thompson, U.S. Pat. Nos. 5,902,880 and 6,146,886 and others described above).

The recombinant vectors capable of expressing the siRNA molecules can be delivered as described above, and persist in target cells. Alternatively, viral vectors can be used that provide for transient expression of nucleic acid molecules. Such vectors can be repeatedly administered as necessary. Once expressed, the siRNA molecule interacts with the target mRNA and generates an RNAi response. Delivery of siRNA molecule expressing vectors can be systemic, such as by intravenous or intramuscular administration, by administration to target cells explanted from a subject followed by reintroduction into the subject, or by any other means that would allow for introduction into the desired target cell.

Diagnostic Methods

A method is also provided herein for detecting Brachyury in a biological sample. The method includes contacting the sample with one or more of an antibody that specifically binds Brachyury to form an antibody-Brachyury complex. The presence or absence of the complex is detected. The methods are of use to improve the confidence of a tissue diagnosis, such as to confirm a diagnosis, or to determine the origin of a tumor. Thus, the method disclosed herein can be used to confirm the diagnosis of a tumor of the small intestine, stomach, kidney, bladder, uterus, ovaries, testes lung, colon and prostate tumors. The methods disclosed herein can be used to confirm the diagnosis of a B cell tumor, such as chronic lymphocytic leukemia (CLL), Epstein-Barr virus transformed B cells, Burkitt's and Hodgkin's lymphomas. The methods disclosed herein can also be used to determine if the origin of a tumor, such as to determine if a metastatic cancer is of small intestine, stomach, kidney, bladder, uterus, ovaries, testes lung, colon, prostate or B cell origin.

In addition, expression of Brachyury is associated with epithelial-to mesenchymal transition. Thus, the methods disclosed herein can be used to determine the likelihood of tumor cell migration and invasion.

The methods can include selecting a subject in need of diagnosis, such as a subject with a tumor, and obtaining a sample from this subject. In several examples, the methods include selecting a subject with a tumor of the small intestine, stomach, kidney, bladder, uterus, ovaries, testes lung, colon or prostate, and obtaining a sample from this subject. In additional examples, the method includes selecting a subject with a tumor of B cell origin, such as chronic lymphocytic leukemia (CLL), a B cell lymphoma, Burkitt's lymphoma or a Hodgkin's lymphoma, and obtaining a sample from this subject.

The sample can be any sample, including, but not limited to, tissue from biopsies, autopsies and pathology specimens. Biological samples also include sections of tissues, such as frozen sections taken for histological purposes. Biological samples further include body fluids, such as blood, serum, spinal fluid or urine. A biological sample is typically obtained from a mammal, such as a rat, mouse, cow, dog, guinea pig, rabbit, or primate. In one embodiment, the primate is macaque, chimpanzee, or a human. In some embodiments, a histological section is utilized, and an immunohistochemical assay is performed.

Antibodies that specifically bind Brachyury are known in the art. Antibodies include polyclonal and monoclonal antibodies. In some embodiments, an antibody fragment, such as an Fv fragment is utilized. In a further embodiment, the antibody is labeled (such as with a fluorescent, radioactive, or an enzymatic label). In additional examples, the antibodies can be conjugated to compounds including, but not limited to, enzymes, magnetic beads, colloidal magnetic beads, haptens, fluorochromes, metal compounds or radioactive compounds.

Methods of determining the presence or absence of a protein are well known in the art. Assays of use include, but are not limited to, radioimmunoassays (RIAs), enzyme linked immunosorbent assays (ELISA), or immunohistochemical assays. The method for detecting Brachyury in a biological sample generally includes the steps of contacting the biological sample with an antibody which specifically reacts, under immunologically reactive conditions, to Brachyury. The antibody is allowed to specifically bind under immunologically reactive conditions to form an immune complex, and the presence of the immune complex (bound antibody) is detected directly or indirectly. A control cell, such as a non-transformed cell or section of the same tissue type, can be included as a control.

Reagents for the Detection of Cells that Express CD8 (CD8+) Cells that Specifically Bind Brachyury Reagents are provided herein for the detection of CD8 expressing cells that specifically bind Brachyury. These reagents are tetrameric MHC Class I/immunogenic Brachyury polypeptide complexes. These tetrameric complexes include an immunogenic Brachyury polypeptide that includes at most twelve consecutive amino acids, wherein the isolated polypeptide comprises the amino acid sequence set forth as WLLPGTSTX$_1$ (SEQ ID NO: 3), wherein X$_1$ is a leucine (L) or a valine (V). Specific examples of immunogenic Brachyury polypeptide that are ten amino acids in length are disclosed above. The tetrameric complexes disclosed herein do not include additional consecutive amino acids of Brachyury (SEQ ID NO: 1), such that the polypeptide does not include the full length Brachyury amino acid sequence.

Tetrameric MHC Class I peptide complexes can be synthesized using methods well known in the art (Altmann et al., Science 274:94, 1996, which is herein incorporated by reference). In one specific non-limiting example, purified HLA heavy chain and β2-microglobulin (β2m) can be synthesized by means of a prokaryotic expression system. One specific, non-limiting example of an expression system of use is the pET system (R&D Systems, Minneapolis, Minn.). The heavy chain is modified by deletion of the trans-membrane and cytosolic tail and COOH-terminal addition of a sequence containing the biotin protein ligase (Bir-A) enzymatic biotinylation site. Heavy chain, β2m, and peptide are then refolded. The refolded product can be isolated by any means known in the art, and then biotinylated by Bir-A. A tetramer is then produced by contacting the biotinylated product with strepavidin.

In one embodiment, the strepavidin is labeled. Suitable labels include, but are not limited to, enzymes, magnetic beads, colloidal magnetic beads, haptens, fluorochromes, metal compounds, radioactive compounds or drugs. The enzymes that can be conjugated to strepavidin include, but are not limited to, alkaline phosphatase, peroxidase, urease and β-galactosidase. The fluorochromes that can be conjugated to the strepavidin include, but are not limited to, fluorescein isothiocyanate, tetramethylrhodamine isothiocyanate, phycoerythrin, allophycocyanins and Texas Red. For additional fluorochromes that can be conjugated to strepavidin, see Haugland, R. P., *Molecular Probes: Handbook of Fluorescent Probes and Research Chemicals* (1992-1994). The metal compounds that can be conjugated to the strepavidin include, but are not limited to, ferritin, colloidal gold, and particularly, colloidal superparamagnetic beads. The haptens that can be conjugated to the strepavidin include, but are not limited to, biotin, digoxigenin, oxazalone, and nitrophenol. The radioactive compounds that can be conjugated to strepavidin are known to the art, and include but are not limited to technetium 99m ($^{99}$Tc), $^{125}$I and amino acids comprising any radionuclides, including, but not limited to, $^{14}$C, $^{3}$H and $^{35}$S. Generally, strepavidin labeled with a fluorochrome is utilized in the methods disclosed herein.

In one embodiment, suspension of cells including T cells that specifically recognize Brachyury is produced, and the cells are reacted with the tetramer in suspension. In one embodiment, these reagents are used to label cells, which are then analyzed by fluorescence activated cell sorting (FACS). A machine for FACS employs a plurality of color channels, low angle and obtuse light-scattering detection channels, and impedance channels, among other more sophisticated levels of detection, to separate or sort cells. Any FACS technique can be employed as long as it is not detrimental to the detection of the desired cells. (For exemplary methods of FACS see U.S. Pat. No. 5,061,620.)

The disclosure is illustrated by the following non-limiting Examples.

EXAMPLES

Example 1

Materials and Methods

Computer-based differential display (CDD) analysis. Comparison of all EST clusters on the human Unigene Built 171 (see the NCBI Unigene website, available on the internet)

was conducted by using the HSAnalyst program as previously described (Baronova et al., FEBS Lett 508(1):143-8, 2001). Unigene EST cluster Hs.389457 corresponds to accession number NM_003181.

Source of cDNA. Expression in normal tissues was studied by using Multiple Tissue cDNA (MTC) panels containing sets of normalized cDNAs from pooled normal tissues from several individuals (Clontech, Mountain View, Calif.). The following panels were used: human MTC Panel I, Panel II, and Blood Fractions Panel. Commercially available tumor tissue-derived cDNAs, prepared from different individuals with different tumor types, were obtained from BioChain Institute Inc. (Hayward, Calif.). Total RNA from human cancer cell lines and normal CD19+ isolated B cells were prepared by using the RNAeasy extraction kit (Qiagen Inc., Valencia, Calif.).

PCR analysis. PCR amplification of cDNA panels was carried out with the following primers specific for NM_003181:

```
E7F 5'-GGGTGGCTTCTTCCTGGAAC-3'      (SEQ ID NO: 4)
and

E7R 5'-TTGGAGAATTGTTCCGATGAG-3'.    (SEQ ID NO: 5)
```

G3PDH specific primers were:

```
forward
5'-TGAAGGTCGGAGTCAACGGATTTGGT-3',   (SEQ ID NO: 6)

reverse
5'-CATGTGGGCCATGAGGTCCACCAC-3'.     (SEQ ID NO: 7)
```

The following conditions were used: 1 minute at 95° C., 35 cycles consisting of 30 sec at 95° C., 30 sec at 58°, and 1 minute at 72° C., and 5 minutes elongation at 72° C. The expected size for the Brachyury and G3PDH products was 172 and 983 bp, respectively. Total RNA derived from human cancer cell lines and normal CD19+ isolated B cells were amplified by using the TITANIUM One-Step RT-PCR kit (Clontech), following the manufacturer's instructions. Primer sequences were as follow:

```
Brachyury,
                                    (SEQ ID NO: 8)
E3F 5'-ACTGGATGAAGGCTCCCGTCTCCTT-3',
and (SEQ ID NO: 9)
E8R 5'-CCAAGGCTGGACCAATTGTCATGGG-3'
```

(Edwards et al., Genome Res 6(3):226-33, 1996); and

β-actin, forward 5'-ATCTGGCACCACACCTTCTA-CAATGAG-3' (SEQ ID NO: 10), and reverse 5'-CGTGGTG-GTGAAGCTGTAGCCGCGCTC-3' (SEQ ID NO: 11). The expected size of the PCR products was 568 bp and 356 bp, respectively.

RT-PCR amplification from NCI-H460 cells: Total RNA was prepared from stably transfected NCI-H460 cells containing a control shRNA plasmid or a Brachyury-specific shRNA construct (Br. shRNA clones 1 and 2) by using the RNeasy extraction kit (Qiagen Inc., Valencia, Calif.), following the manufacturer's recommendations. Five ng of total RNA were amplified by using the TITANIUM One-Step RT-PCR kit (Clontech, Mountain View, Calif.), following the manufacturer's instructions. Primer sequences were as follows: Brachyury, E3F 5'-ACTGGATGAAGGCTC-CCGTCTCCTT-3' (SEQ ID NO: 8), and E8R 5'-CCAAG-GCTGGACCAATTGTCATGGG-3' (SEQ ID NO: 9); and β-actin, forward 5'-ATCTGGCACCACACCTTCTACAAT-GAG-3' (SEQ ID NO: 10), and reverse 5'-CGTGGTGGT-GAAGCTGTAGCCGCGCTC-3' (SEQ ID NO: 11). The expected size of the PCR products was 568 and 356 bp, respectively.

Cell cultures. The human carcinoma cell lines were maintained free of *Mycoplasma* in RPMI 1640 medium (Invitrogen, Carlsbad, Calif.) supplemented with 10% fetal bovine serum, 2 mM glutamine, and 1× solution of antibiotic/antimycotic (Invitrogen). Additional cell lines used in this study were the C1R-A2 cell line, which is a human B-cell lymphoblastoid line transfected to express surface HLA-A2 antigen (Shimojo et al., J Immunol 143(9):2939-47, 1989), and the T2 (HLA-A2+) transport-deletion mutant cell line (Salter et al., Embo J 5(5):943-9, 1986).

Peptides. The computer algorithm from the Bioinformatics and Molecular Analysis Section of NIH (BIMAS) developed by Parker et al. was used (Parker et al., J Immunol 152(1): 163-75, 1994, incorporated by reference herein). A panel of 9-mer and 10-mer peptides (see Table 2, below) was synthesized at >90% purity (Biosynthesis, Lewisville, Tex.). The CEA peptide CAP 1-6D (YLSGADLNL, SEQ ID NO: 12), the HIV peptide (ILKEPVHGV, SEQ ID NO: 13), and a CEA peptide specific for HLA-A3 were used as controls.

HLA-A2 binding assay. Binding of Brachyury-specific peptides T-p1, T-p2, T-p3, and T-p4 (SEQ ID NOs: 1-4) to HLA-A0201 molecules was evaluated by flow cytometry analysis of HLA-A02 surface expression on T2 cells. T2 cells ($1\times10^6$) in serum-free Iscove's modified Dulbecco's medium were incubated in the presence of various concentrations of each peptide, in 24-well culture plates at 37° C. with 5% $CO_2$. After 18 hours in culture, T2 cells were harvested, washed with 1× phosphate buffered saline (PBS) (Invitrogen) and stained with 20 μl of a FITC-conjugated anti-HLA-A02-specific monoclonal antibody (MAb) (One Lambda, Inc., Canoga Park, Calif.). A FITC-conjugated IgG2a MAb (BD Biosciences, San Jose, Calif.) was used as an isotype control. Data acquisition and analysis were conducted on a FACS-Calibur™ system using the CELLQueSt™ software (BD Biosciences). Results were expressed as mean fluorescence intensity (MFI) collected on a log scale. To measure the half-life of major histocompatibility complex (MHC)-peptide complexes, T2 cells were incubated for 18 hours in the presence of 25 μM of each peptide, subsequently washed free of unbound peptides and incubated for various time points in presence of 10 μg/ml of Brefeldin A. Flow cytometry was conducted as described above. Assuming first order kinetics, the $\log_2$ of $MFI/MFI_0$ (MFI is the fluorescence at each time point and $MFI_0$ the initial fluorescence at time 0) was plotted against time (minutes). The decay rate constant was calculated as the slope of the linear regression for each curve and the half-life of each peptide-MHC complex was calculated as the inverse of the ratio 1/decay rate constant.

Culture of DCs from Peripheral Blood Mononuclear cells (PBMCs). Peripheral blood used in this study was collected from healthy donors and cancer patients. Peripheral blood mononuclear cells (PBMCs) were isolated from leukapheresis samples by centrifugation on a Ficoll density gradient (LSM Lymphocyte Separation Medium, ICN Biochemicals Inc., Aurora, Ohio). For the preparation of dendritic cells (DCs), PBMCs were resuspended in AIM-V medium (Invitrogen) and allowed to adhere to the surface of T-150 flasks (Corning Costar Corp., Cambridge, Mass.). After 2 hours at 37° C., the non-adherent cell fractions were removed and the adherent cells were cultured in AIM-V medium containing 100 ng/ml of recombinant human GM-CSF (rhGM-CSF) and 20 ng/ml of recombinant human IL-4 (rhIL-4) for 7 days.

Generation of T-cell lines. To generate Brachyury-specific cytotoxic T cells (CTLs), peptide-pulsed irradiated (30 Gy) DCs were used as antigen presenting cells (APCs) with autologous, non-adherent cells used as effector cells at an effector-to-APC ratio of 10:1. Cultures were maintained for three initial days in medium containing 10% human AB serum, and four additional days in the same medium supplemented with 20 U/ml of recombinant human IL-2. After a seven-day culture period, designated as an in vitro stimulation (IVS) cycle, cells were re-stimulated as described above.

Detection of cytokines. After three IVS cycles, CD8+ T cells that were negatively isolated by using a CD8+ isolation kit (Miltenyi Biotec, Auburn, Calif.) were stimulated for 24 hours in the presence of peptide-pulsed autologous DCs. Culture supernatants were analyzed for the presence of IFN-γ by using an enzyme linked immunosorbant assay (ELISA) kit (Biosource International Inc., Camarillo, Calif.). Results were expressed in pg/ml.

Cytotoxic assay. Target cells were labeled with 50 µCi of $^{111}$Indium-labeled oxyquinoline (Amersham Health, Silver Spring, Md.) for 15 minutes at room temperature. Target cells in medium containing 10% human AB serum were plated at $3 \times 10^3$ cells per well, in 96-well rounded-bottom culture plates. Labeled C1R-A2 or T2 cells were incubated with peptides at the indicated concentrations for 60 minutes at 37° C. in 5% $CO_2$ before the addition of effector cells. No peptide was added when carcinoma cells or CD19+ B cells were used as targets. CD8+ T cells negatively isolated from T-cell cultures were used as effector cells, at various effector-to-target (E:T) cell ratios. When target cells were C1R-A2 or T2, co-cultures were incubated at 37° C. in a 5% CO2 atmosphere for 6 hours as previously described (Tsang et al., Clin Cancer Res 11(4):1597-607, 2005); when carcinoma cell lines were used as targets, co-cultures were incubated as previously described (Tsang et al., supra) in the same conditions for a period of 16 hours. Cytotoxic assays employing normal donor CD19+ B cells as targets were conducted for 5 hours as previously described (Palena et al., Blood 106(10):3515-23, 2005), due to the high levels of spontaneous release observed after a 16-hour incubation period. Supernatants were harvested and the $^{111}$In released was measured by gamma counting. Spontaneous release was determined by incubating the target cells with medium alone, and complete lysis by incubating the target cells with 2.5% Triton X-100. All determinations were performed in triplicate, and standard deviations were calculated. Specific lysis was calculated as follows: specific lysis (%)=[(observed release−spontaneous release)/(complete release−spontaneous release)]×100.

Generation of stably transfected NCI-H460 cells: The NCI-H460 cell line, originally derived from a patient with a large cell carcinoma of the lung, was obtained from the American Type Culture Collection (ATCC, Manassas, Va.) and maintained in RPMI-1640 medium supplemented with 1× Antibiotic/Antimycotic solution (Invitrogen, Carlsbad, Calif.) and 10% fetal bovine serum (FBS, Gemini Bio-Products West Sacramento, Calif.). Cells ($1 \times 10^6$) were transfected using the nucleofector device and technology (Amaxa Biosystems, Gaithersburg, Md.) with 1 µg of purified, linearized DNA plasmid encoding for a non-targeting shRNA (designated as control shRNA) or two Brachyury-specific targeting shRNA constructs (designated as Br. shRNA clones 1 and 2), following the recommendations of the manufacturers. After 48 hours in culture, stably transfected cells were selected in RPMI-1640 medium containing 10% FBS and 1 µg/ml of puromycin (Sigma Aldrich, St. Louis, Mo.).

Western Blot analysis of mesenchymal and epithelial markers: Protein extracts were prepared from NCI-H460 cells stably transfected with the control shRNA and Brachyury-specific shRNA (clone 2) by using the Ripa Lysis Buffer kit (Santa Cruz Biotech, Santa Cruz, Calif.) following the manufacturer's instructions. Protein concentration was determined by using the BCA Protein Assay kit (Thermo Scientifics, Rockford, Ill.).

Ten micrograms (mg) of proteins from each sample were resolved on 4-12% polyacrylamide gradient pre-cast gels and subsequently transferred to nitrocellulose membranes (Invitrogen). Blots were blocked with freshly made 0.5% casein in PBS for 1 hour at room temperature. Subsequently, blots were probed with 1:500-1:1000 dilution of primary antibodies in 0.5% casein solution overnight at 4° C. Antibodies were anti-human fibronectin, vimentin, g-catenin, and b-actin (BD-Biosciences, San Jose, Calif.). Blots were washed 3 times with PBS and incubated with a 1:5000 dilution of horseradish peroxidase (HRP)-conjugated secondary anti-mouse IgG antibody (Invitrogen) for 1 hour at room temperature. Blots were washed 5 times with PBS/Tween 20 and were developed using the Western Lighting chemiluminescent detection reagent (PerkinElmer, Boston Mass.) and autoradiographs were obtained.

Migration and invasion assays: The migratory abilities of NCI-H460 cells stably transfected with a control shRNA or a Brachyury-specific shRNA (Br.shRNA clone 2) were examined in vitro using Blind Well Chambers (Neuroprobe, Gaithersburg, Md.) with 12 micrometer-pore size polycarbonate filters. Briefly, RPMI-1640 medium containing 10% fetal bovine serum (FBS) was added to the lower chambers, and cells ($1 \times 10^5$ cells, 300 µl in RPMI medium free of serum) to the upper chambers. For the invasion assays, polycarbonate filters were pre-coated with a 1:1 dilution of Matrigel (BD Biosciences) and serum free RPMI-1640 medium. Experiments were conducted in triplicate samples of each cell line. After incubation for 48 hours at 37° C., the upper side of the filters was extensively cleaned with cotton tips, filters were removed from the chambers, fixed, and stain with Diff-Quik stain (Dade Behring Inc., Newark, Del.). The number of cells associated with the lower side of the membranes was evaluated by direct counting of five random 100× objective fields. Each bar represents the results for each replicate assay±SEM.

Example 2

Computer-Based Prediction

In silico profiling of gene expression in the human Unigene Built 171 was conducted as previously described (Baranova et al., FEBS Lett 508(1):143-8, 2001) by using the HSANA-LYST™ software tool. An algorithm executed by the program returned a list of candidate EST clusters that contained >10 ESTs with >90% of the ESTs derived from tumor libraries. Among them, the cluster Hs.389457 contained the whole mRNA sequence encoding for the human Brachyury gene (mouse Brachyury homolog). From a total of 55 ESTs included in this cluster, 50 ESTs corresponded to tumor-derived libraries constructed from lung carcinoma cell lines, germ-cell tumors, chronic lymphocytic leukemia B cells, and breast cancer. Two normal tissue-derived ESTs found in the cluster Hs.389457 belonged to a library constructed from pooled RNA from fetal lung, testis, and normal B cells. The other three ESTs in the cluster were designated as "undefined," since they lacked tissue origin descriptions.

Example 3

Confirmation of Expression

Figure 1B:
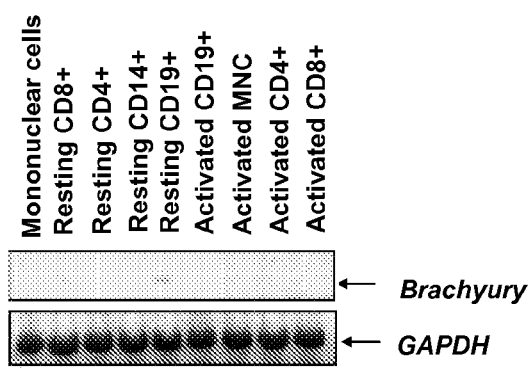

The computer-based predictions of the expression of Brachyury mRNA were then verified by RT-PCR analysis of Brachyury expression in a range of normal and malignant human tissues. Most normal tissue-derived cDNA samples, as predicted by the algorithm, showed no Brachyury mRNA expression (FIGS. 1A and 1B). Very weak signals, however, were observed with cDNA derived from normal testis, spleen (FIG. 1A), and resting CD19+ purified cells (FIG. 1B). These results were also in accordance with the software's prediction that two out of 55 ESTs in the cluster belonged to a library prepared from pooled testis, fetal lung, and normal B lymphocytes.

The expression of Brachyury in normal B cells was further evaluated in CD19+ samples isolated from various healthy donors; weak amplification was observed in four out of nine samples analyzed when using 1 microgram of total RNA and 35 cycles of PCR amplification.

Figure 1C:
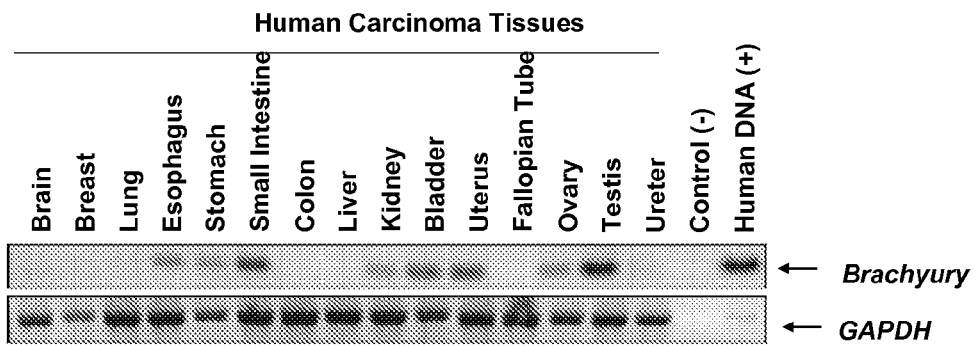

In contrast, RT-PCR amplification of cDNA samples derived from tumor-tissues demonstrated relatively high levels of Brachyury mRNA expression in carcinomas of the esophagus, stomach, small intestine, kidney, bladder, uterus, ovary, and testis (FIG. 1C), and a weak signal in a lung carcinoma-derived sample. PCR products derived from two of the reactions were subsequently sequenced to confirm the gene and rule out the possibility of non-specific amplification. The expression of Brachyury was further analyzed in total RNA derived from 30 human carcinoma cell lines (Table 1).

TABLE 1

RT-PCR expression of human Brachyury in human tumor cell lines

| Tumor type | Tumor cell line | Brachyury mRNA[1] |
|---|---|---|
| Lung | H441 | ++ |
|  | NCI-H460 | ++ |
|  | H226 | + |
|  | NCI-H520 | + |
|  | SW900 | − |
| Colon | SW480 | ++ |
|  | SW620 | ++ |
|  | Colo 201 | + |
|  | Colo 205 | + |
|  | CaCo2 | + |
|  | SW403 | + |
|  | T-84 | + |
|  | SW948 | − |
|  | SW1463 | − |
|  | HT-29 | − |
|  | SW1116 | − |
| Prostate | LNCAP | + |
|  | PC-3 | + |
|  | DU145 | + |
| Pancreatic | Capan-2 | + |
|  | Paca-2 | − |
|  | BxPC3 | − |
|  | PANC-1 | − |
|  | ASPC-1 | − |
| Breast | MCF-7 | − |
|  | MA-MB-231 | − |
| Ovarian | SW626 | ++[a] |
|  | NIH-OVCAR3 | − |
|  | SK-OV3 | − |
| Osteosarcoma | U2OS | − |

[1]Expression of Brachyury mRNA is shown relative to the expression of β-actin as being negative (−), positive (+), or strongly positive (++).
[a]There is conflicting evidence that this cell line may be of colonic origin. See Furlong et al., J Natl Cancer Inst 91 (15): 1327-8, 1999.

Brachyury mRNA expression was observed in most of the lung cancer-derived, colon cancer-derived, and prostate cancer-derived tumor cell lines (Table 1). These results thus validated the CDD predictions through RT-PCR and confirmed expression of Brachyury in several tumors but not in normal tissues.

Reverse transcriptase polymerase chain reaction (RT-PCR) analysis demonstrated Brachyury expression in tumors of the small intestine, stomach, kidney, bladder, uterus, ovary, and testis, as well as in cell lines derived from lung, colon, and prostate carcinomas, but not in the vast majority of the normal tissues tested. Elevated Brachyury mRNA expression was also detected in most of the B-cell malignancies examined, including chronic lymphocytic leukemia (CLL) cells, Epstein-Barr virus (EBV)-transformed B-cell lines, Burkitt's and Hodgkin's lymphoma cell lines. Quantitative real-time PCR analysis showed elevated expression of Brachyury mRNA in CD19+ cells isolated from 13/25 CLL patients, as compared with very low, if any, level of expression in B lymphocytes isolated from peripheral blood from healthy donors or a panel of normal human tissues. A time-course infection of normal B-lymphocytes with EBV showed that Brachyury mRNA expression is induced as early as 48 hours post-infection and is maintained in long-term cultures of transformed B-cell lines. EBV, a lymphotropic human herpesvirus, is linked to various clinical disorders including human neoplasms of hematological origin such as lymphomas in immunocompromised individuals and posttransplant lymphoproliferative disorders, and those of epithelial origin such as nasopharyngeal carcinomas and gastric adenocarcinomas. These results suggest that Brachyury is a potential tumor target for hematological malignancies of B-cell origin and, in particular, for EBV-associated malignancies. The results also demonstrate that elevated Brachyury expression (as compared to a control cell of the same tissue type) serves as a marker for confirmation of diagnosis of tumors of these types. In addition to improving the confidence with which a tissue diagnosis of the cancers is made, the detection of Brachyury over-expression in a metastatic lesion helps identify potential sites of primary tumor so that further diagnostic tests of these potential sites can be more cost effectively conducted and therapy (such as surgical excision of the primary tumor) more quickly achieved. Hence detection of Brachyury can be used in methods of diagnosing and treatment of cancers characterized by Brachyury expression.

Example 4

Production of Brachyury Immunogenic Peptides that Bind MHC

The amino acid sequence of the Brachyury protein was then analyzed for HLA-A0201 peptide-binding prediction by using a computer algorithm from BIMAS. The top-ranking candidate peptides generated by the program, including three 9-mers and a 10-mer whose amino acid sequences and algorithm scores are presented in Table 2, were selected for further studies.

TABLE 2

HLA-A020 1 peptide motif
search using BIMAS software

| Peptide | Residues | Start position* | Sequence | Score† |
|---------|----------|-----------------|----------|--------|
| T-p1 | 9-mer | 345 | SQYPSLWSV (SEQ ID NO: 14) | 389.26 |
| T-p2 | 9-mer | 246 | WLLPGTSTL (SEQ ID NO: 15) | 363.59 |
| T-p3 | 9-mer | 422 | RLIASWTPV (SEQ ID NO: 16) | 118.24 |
| T-p4 | 10-mer | 86 | AMYSFLLDFV (SEQ ID NO: 17) | 996.36 |

*Staff position corresponds to the amino acid position in the protein sequence.
†Estimate of half-time disassociation of a molecule containing this subsequence.

Figure 2A:
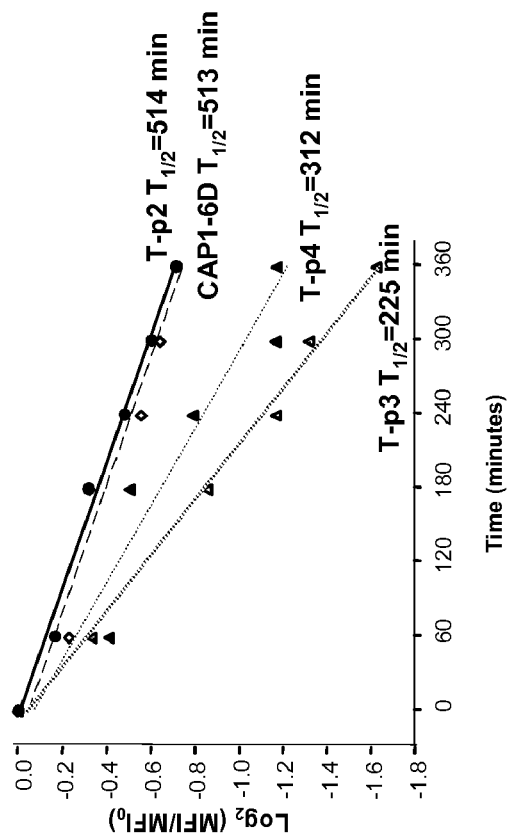
FIGS. 2A-2B are graphs illustrating the binding of predicted peptides to HLA-A0201 molecules.
Figure 2B:
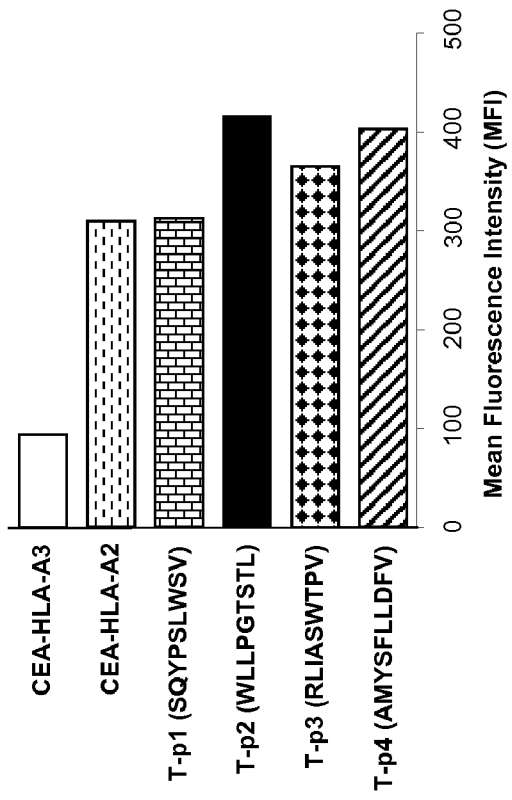

In silico-predicted epitopes were then assessed for binding to the MHC molecules in a cell-based assay. TAP-deficient T2 (HLA-A2+) cells were incubated in the presence of 25 μM of each peptide and subsequently tested for cell surface MHC-stabilization by bound peptides. Flow cytometry staining of HLA-A02 (FIG. 2A) demonstrated that all four candidate peptides predicted by the algorithm efficiently bound to HLA-A02 molecules when compared to positive and negative control peptides. Peptides with the highest binding to T2 cells (T-p2, T-p3, and T-p4) were selected for further studies. The half-life of each peptide-MHC complex was determined; T2 cells were incubated overnight in the presence of 25 μM of each peptide followed by the addition of brefeldin A and subsequent evaluation of cell surface staining of HLA-A02 at various time points. MHC-peptide complexes involving Tp-2 have a half-life of 514 minutes, similar to that of the positive control peptide (CAP 1-6D). In contrast, MHC-peptide complexes involving T-p3 and T-p4 showed shorter half-lives of 225 and 312 minutes, respectively (FIG. 2B).

Example 5

Immunogenicity

Once the ability of the predicted peptides to bind HLA-A02 molecules was demonstrated, the immunogenicity of peptides T-p2, T-p3, and T-p4 was investigated by evaluating their ability to induce specific CTLs in vitro. Irradiated DCs pulsed with 25 μM of each peptide were used to stimulate autologous T cells from a healthy donor's PBMCs. After three in vitro stimulations (IVS), isolated CD8+ T cells were subsequently stimulated for 24 hours in the presence of autologous DCs alone or DCs pulsed with each of the "inducer" peptides (T-p2, T-p3, or T-p4) or an irrelevant HIV-peptide. Of the three peptides tested, T-p2 and T-p3 induced antigen-specific CTLs able to release IFN-γ upon stimulation with the specific peptide (FIG. 3A). Both CTL lines were then tested for their cytotoxic activity against peptide-pulsed HLA-A0201+ targets. As shown in FIG. 3B, only T cells generated with the T-p2 peptide were able to specifically lyse peptide-pulsed target cells, consistent with the peptide's ability to form stable MHC complexes compared with T-p3 and T-p4. Titration of the cytotoxic activity of the T-p2 CTLs showed cytotoxic responses at peptide concentrations as low as 1 nM (FIG. 3C). Cytotoxic lysis of normal B lymphocytes was also analyzed since low expression of Brachyury was detectable in CD19+ cells isolated from various healthy donors. No lysis was observed with any of the normal B cells analyzed from five different healthy donors.

Figure 4A:
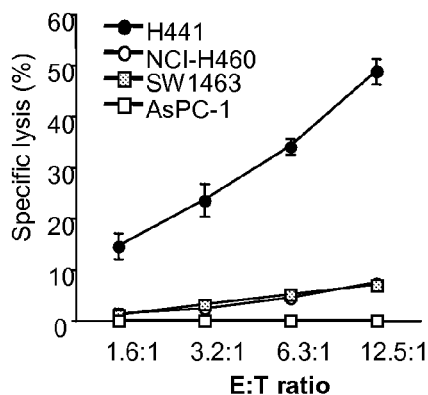
FIGS. 4A-4F are graphs showing the Cytotoxic activity of Brachyury-specific CTLs against tumor targets.
Figure 4B:
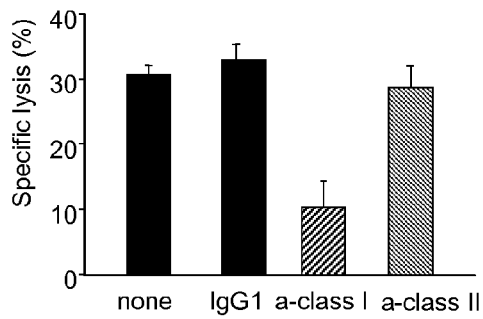

The cytolytic activity of the T-p2-specific CTLs was then tested against several tumor targets. Tumor cell lines used as targets included the lung carcinoma cells H441 (HLA-A0201+/T antigen+) and NCI-H460 (HLA-A24, 68+/T antigen+), the colorectal carcinoma line SW1463 (HLA-A0201+/T antigen−), and the pancreatic carcinoma cells AsPC-1 (HLA-A02−). CTLs derived with the T-p2 epitope were highly efficient at killing H441 tumor cells, while no lysis was observed against the other cell lines. MHC-restriction was shown by the observation that the H460 tumor cell line that is highly positive for Brachyury but HLA-A0201 negative was not killed by the Tp-2 CTLs (FIG. 4A). Conversely, the tumor cell line SW1463 served as an antigen-specific control, since it is negative for the expression of Brachyury but positive for the expression of HLA-A0201. Similarly, the control AsPC-1 (HLA-A0201−) cells were also not killed by the Brachyury-specific T cells. These results indicate that T cells that have been expanded in vitro in the presence of the T-p2 peptide are able to specifically lyse those tumor cells that express Brachyury within the correct MHC-class I context. As shown in FIG. 4B, T-p2 CTLs-mediated killing of H441 tumor cells was blocked by antibodies directed against the MHC-class I molecules but not the MHC-class II molecules, further confirming the MHC-class I restriction of the observed lysis.

The Tp-2 peptide was then tested for in vitro expansion of Brachyury-specific T cells from PBMC of four additional healthy donors. Tp-2-specific CTLs were induced from two out of five healthy donors tested.

Figure 4C:
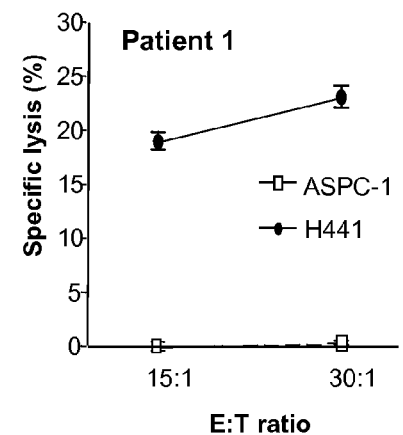
Figure 4D:
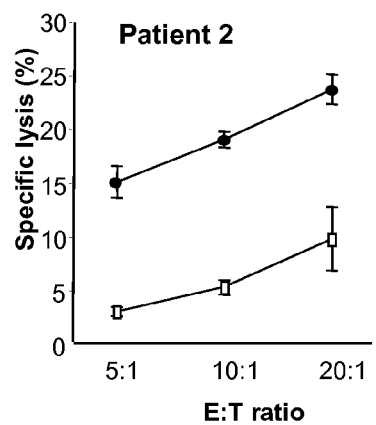
Figure 4E:
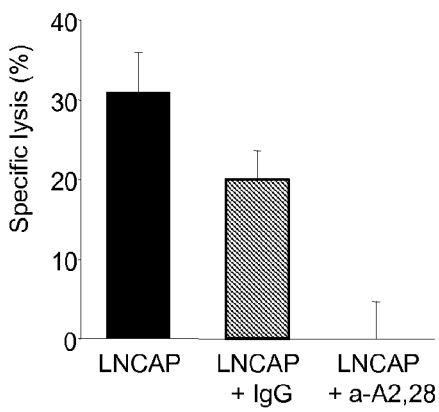
Figure 4F:
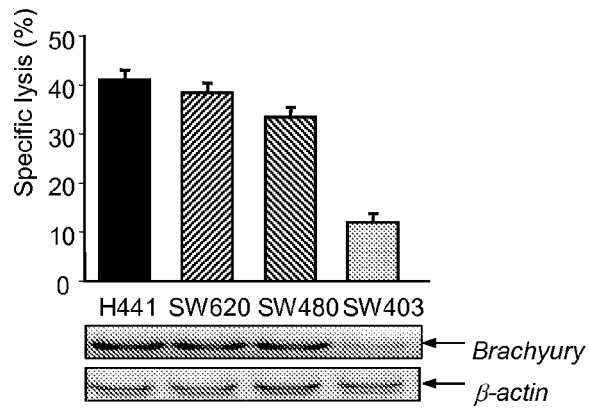

Generation of T-p2 specific CTLs was also successfully carried out from PBMCs of two cancer patients. T cells isolated from PBMCs of a colorectal cancer patient (designated as patient 1) and an ovarian cancer patient (designated as patient 2) were stimulated in vitro for three cycles in the presence of autologous, irradiated T-p2-pulsed DCs as described in Example 1. CD8+ T cells negatively isolated from these cultures were assayed for cytotoxic activity against tumor cells. As shown in FIGS. 4C and 4D, after three IVS both CTL lines were able to lyse H441 tumor cells. After five IVS, CTLs derived from both patients were tested for their ability to lyse additional tumor cell lines positive for the expression of Brachyury. As shown in FIG. 4E, T-p2-specific CTLs derived from patient 1 were able to lyse LNCAP cells (HLA-A2+/Brachyury+) in an HLA-A02 restricted way, as denoted by the blocking of cytotoxic killing in presence of anti-HLA-A02 but not in presence of a control IgG. FIG. 4F shows that T-p2 cells expanded from the blood of patient 2 were able to lyse H441, SW620, and SW480 tumor cells, all of them being Brachyury+ and HLA-A2+. On the other hand, lysis of SW403 cells, which are HLA-A2+ and express lower levels of Brachyury mRNA (FIG. 4E), was only minimal. Altogether, Tp-2 cells derived from healthy individuals and cancer patients were able to lyse 4/5 Brachyury positive tumors, while no lysis was observed for control tumor cells that were (a) HLA-A2−/Brachyury+ (NCI-H460), or (b) HLA-A2+/Brachyury− (SW1463).

In conclusion, the results demonstrated that T-p2-specific T cells generated from both healthy donors and cancer patients were able to recognize and mediate cytotoxic lysis of tumor cells that endogenously express the Brachyury protein.

As demonstrated herein, high-throughput gene expression analysis in tumors versus normal tissues constitutes a relatively new approach for the identification of therapeutic cancer targets. Computer programs have been emerging for mining of EST databases that use publicly available information from the vast collection of ESTs (Scheurle et al., Cancer Res 2000, 60(15):4037-4043). As the frequency of ESTs in a cDNA library appears to be proportional to the abundance of associated transcripts in the tissue from which the library was prepared (Audic and Clayerie, Genome Res 1997; 7:986-995), data on ESTs expression can be correlated with tissue-related or disease-related gene expression signatures. In the present studies, data mining software tool (HSANALYST™) was successfully used for the identification of Unigene EST cluster Hs.389457, corresponding to the human gene Brachyury, as a tumor antigen, and validated the in silico prediction by RT-PCR in a set of normal and tumor tissues and cancer cell lines. Expression of Brachyury was shown to be elevated in tumors of the small intestine, stomach, kidney, bladder, uterus, ovary, and testis, and in the majority of cell lines derived from lung, colon, and prostate carcinomas. Because of the high grade of conservation among members of the T-box family, BLAST analysis of the primers sequence was conducted to discard any possible amplification of sequences derived from other members of the T-box family, and the fidelity of the amplified band was confirmed by DNA sequencing. The high levels of expression of Brachyury in tumors contrasted with its lack of expression in most normal adult tissues, with the exception of low levels observed in testis, spleen, and CD19+ (resting) lymphocytes. Without being bound by theory, the weak signal in spleen could be attributable to the presence of CD19+ cells.

The affinity prediction method from BIMAS was applied in the studies presented herein for identifying Brachyury peptides with high affinity binding for HLA-A0201. All four top-ranked peptides effectively bound to HLA-A0201 molecules, although peptide-MHC complexes showed differences in their decay rate. Tp-2 was the only peptide, however, able to expand CTLs in vitro that are capable of releasing IFN-γ in response to peptide-specific stimulation and lysing peptide-pulsed targets with high efficiency. This peptide also showed the maximum stability of binding to HLA-A0201, which could result in increased immunogenicity.

The lung carcinoma cell line H441 was effectively lysed in the presence of Brachyury-specific CTLs even at a low ratio of effector T cells-to-targets, in an antigen-specific and MHC-restricted manner. Furthermore, it was demonstrated that Brachyury-T-p2-specific CTLs can be expanded in vitro from PBMCs of a colorectal cancer patient and an ovarian carcinoma patient, demonstrating that Brachyury is of use as a therapeutic target for cancer vaccine regimens. Thus, it has been demonstrated that (a) a T-box transcription factor and (b) a molecule implicated in mesodermal development, (such as epithelial-to mesodermal transition, EMT), can be a potential target for human T-cell mediated cancer immunotherapy.

Example 6

Stable Knockdown of Brachyury Expression Induces a Mesenchymal-to-Epithelial Transition in NCI-H460 Lung Carcinoma Cancer Cells In order to evaluate whether Brachyury plays a role on modulating the epithelial-to-mesenchymal (EMT) program, Brachyury expression was stably silenced in NCI-H460 lung carcinoma cells that normally express high levels of Brachyury mRNA. RT-PCR analysis confirmed the silencing of Brachyury expression in cells transfected with the Brachyury-specific shRNA clones 1 and 2, as compared with cells transfected with the non-targeting shRNA control construct (FIG. 5A), with the clone 2 showing a higher level of silencing of Brachyury expression.

Western blot analysis of expression of various epithelial and mesenchymal markers showed that silencing of Brachyury expression resulted in marked decreases on the expression of fibronectin and vimentin, both markers of a mesenchymal phenotype. The expression of the epithelial marker γ-catenin, on the other hand, was enhanced as a result of Brachyury's silencing. Therefore, at the biochemical level, silencing of Brachyury expression in NCI-H460 cells repressed expression of mesenchymal markers and concomitantly elicited expression of epithelial markers, changes typically observed during a mesenchymal-to-epithelial (MET) transition.

Example 7

Figure 6:
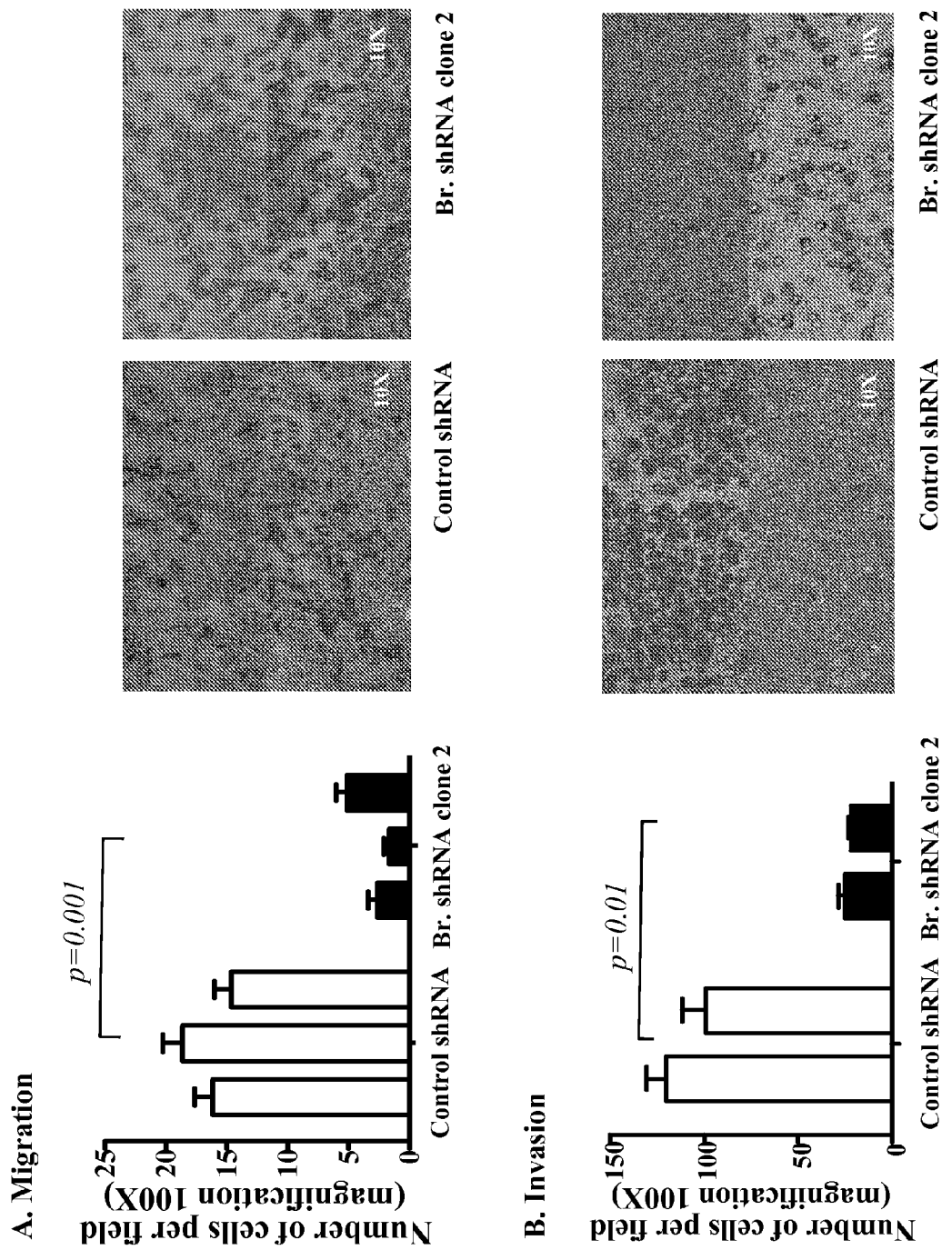
FIGS. 6A-6B are digital images and bar graphs showing that the loss of Brachyury impairs the migratory and invasive properties of NCI-H460 lung carcinoma cells in vitro. In vitro assay of (FIG. 6A) cell migration and (FIG. 6B) cell invasion in NCI-H460 lung carcinoma cells stably transfected with a control shRNA or a Brachyury-specific shRNA construct (Br.shRNA clone 2). Experiments (n=3) were conducted in triplicate samples of each cell line as described in the Examples section. The graph shows results from one representative experiment. Each bar represents the results for an individual replicate assay±SEM. Representative images of the bottom side of the filters for each cell line under X10 magnification are also shown. Statistical analysis of Student's t-test was performed.

Loss of Brachyury Impairs the Migratory and Invasive Properties of NCI-H460 Lung Carcinoma Cells In Vitro Boyden-chamber transwell assays were also performed in order to determine whether Brachyury expression in NCI-H460 cells modulates the migratory and invasive characteristics of these cells. As shown in FIG. 6, NCI-H460 cells stably silenced for Brachyury expression (Br. shRNA clone 2) showed a significant reduction on their migratory ability (FIG. 6A) as well as a marked reduction on their ability to degrade and invade the extracellular matrix (FIG. 6A). These results support the conclusion that the T-box transcription factor Brachyury can serve as a modulator of the mesenchymal phenotype of tumor cells and could program metastasis-associated cellular qualities.

Example 8

Expression of Brachyury in Hematological Malignancies

The expression of Brachyury in chronic lymphocytic leukemia (CLL) as well as other hematological malignancies (Hodgkin's lymphoma, non-Hodgkin's lymphoma, Burkitt's lymphoma) was investigated. CD19+ cell were isolated from CLL patients. The relative expression of Brachyury in CD19+ B cells was evaluated by quantitative real-time polymerase chain reaction (PCR), using primers to human Brachyury and GAPDH. The expression of Brachyury in CD19+ cells isolated from CLL patients was 0.318+/−0.752, while the expression of Brachyury in healthy donors was 0.019+/−0.023. It was also demonstrated that Brachyury was expressed on CD5+CD19+ leukemia cells. Using reverse-transcriptase PCR(RT-PCR) Brachyury was detected in EBV transformed B Cell lines, (B-EBV 701, B-EBV 1383, C1R) as well as in Burkitt's lymphoma (DAUDI and RAJI) and Hodgkin's lymphoma (RPMI 6666) cell lines.

B lymphocytes from healthy donors were infected in vitro with EBV supernatants. The RNA was isolated over time and analyzed for Brachyury expression (by RT-PCR). Brachyury was expressed at 72 and 96 hours following EBV infection. In the tree subject tested, Brachyury expression also could be detected six days after EBV infection.

Thus, elevated expression of Brachyury mRNA was detected in CD19+ cells from CLL patients as compared to CD19+ cells from healthy donors. 13/25 CLL patients showed increased levels of Brachyury as compared to normal B cells. No correlation was found between the level of Brachyury expression and the white blood cell count or Rai stage. Expression of Brachyury was also elevated in LCL (EBV-transformed B cell) lines, Burkitt's lymphoma cell lines and the Hodgkin's lymphoma line RPMI16666. EBV infection of normal B lymphocytes resulted in expression of Brachyury mRNA. Brachyury expression could be detected as early as 48 hours after infection; Brachyury expression peaked at 72 hours post-infection.

Example 9

Inhibition of Tumor Growth or Metastasis Using a Specific Binding Agent

This example describes methods that can be used to significantly reduce tumor growth or metastasis in a subject with a tumor of epithelial origin, such as small intestine, kidney, bladder, uterus, ovary or testis, or in carcinomas, such as lung, colon and prostate carcinomas, or in a tumor of B-cell origin, such as chronic lymphocytic leukemia, Burkitt's lymphoma or Hodgkin's lymphoma.

Based upon the teaching disclosed herein, tumor growth or metastasis can be reduced or inhibited by administering a therapeutically effective amount of a composition, wherein the composition comprises a specific binding agent for Brachyury, thereby reducing or inhibiting tumor growth or metastasis in the subject.

In an example, a subject who has been diagnosed with the tumor is identified and selected for treatment. Following subject selection, a therapeutic effective dose of the composition including the specific binding agent is administered to the subject. For example, a therapeutic effective dose of a specific binding agent for Brachyury is administered to the subject to inhibit tumor growth and/or metastasis. In an example, the specific binding agent is a siRNA. In a further example, the specific binding agent is an antisense molecule. The amount of the composition administered to prevent, reduce, inhibit, and/or treat the tumor depends on the subject being treated, the severity of the disorder, and the manner of administration of the therapeutic composition. Ideally, a therapeutically effective amount of an agent is the amount sufficient to prevent, reduce, and/or inhibit, and/or treat the tumor in the subject without causing a substantial cytotoxic effect in the subject.

In one specific example, siRNAs are administered at according to the teachings of Soutschek et al. (*Nature Vol.* 432: 173-178, 2004) or Karpilow et al. (*Pharma Genomics* 32-40, 2004) both of which are herein incorporated by reference in their entireties. In other examples, the subject is administered the therapeutic composition daily for a period of at least 30 days, such as at least 2 months, at least 4 months, at least 6 months, at least 12 months, at least 24 months, or at least 36 months.

Subjects will monitored by methods known to those skilled in the art to determine tumor responsiveness to the siRNA or antisense. It is contemplated that additional agents can be administered, such as antineoplastic agents in combination.

Example 10

Retrospective Study

In order to determine the correlation of Brachyury expression with the prognosis of a tumor, samples of lung, colon, breast, and prostate cancer tissues, among others, are analyzed by real-time PCR to determine the expression of Brachyury mRNA, as described above. Commercially available cDNA panels (TissueScan Real-Time Disease qPCR Arrays, Origene Technologies, Rockville, Md.) containing cDNA prepared from individual tumor samples are tested with Brachyury- and GAPDH-specific PCR primers to obtain a quantitative expression of Brachyury mRNA in each sample. Each cDNA panel includes information on tumor grade and stage (Samples from stages 1A-IV for lung cancer; stages I to IV for prostate cancer; stages I to IV for colon cancer; and stages 0 to IV for breast cancer will be tested, for example). Brachyury mRNA is preferentially expressed in samples of tumors from patients diagnosed to be at higher stages than in samples of tumors from patients diagnosed to be at lower stages.

It will be apparent that the precise details of the methods or compositions described may be varied or modified without departing from the spirit of the described invention. We claim all such modifications and variations that fall within the scope and spirit of the claims below.

We claim:

1. An isolated polypeptide, wherein the isolated polypeptide comprises the amino acid sequence set forth as one of:
   (a) WLLPGTSTX$_1$ (SEQ ID NO: 3), wherein X$_1$ is a leucine (L) or a valine (V);
   (b) SX$_2$YX$_3$SLX$_4$SX$_5$ (SEQ ID NO: 18), wherein X$_2$ and X$_5$ are either a valine or a leucine, wherein X$_3$ is proline (P), serine (S), threonine (T), leucine (L), or valine (V) and wherein X$_4$ is tryptophan (W), valine (V), leucine (L), isoleucine (I), serine (S) or threonine (T);
   (c) WLLX$_6$GTSTX$_7$ (SEQ ID NO: 19), wherein X$_6$ is serine (S), threonine (T), isoleucine (I), or valine (V) and wherein X$_7$ is leucine (L) or valine (V);
   (d) X$_8$LIASWTPV (SEQ ID NO: 20, wherein X$_8$ is one of tyrosine (Y) or tryptophan (W);
   (e) X$_9$LIASX$_{10}$TPV (SEQ ID NO: 21), wherein X$_9$ is an arginine (R), tyrosine (Y) or tryptophan (W) and X$_{10}$ is a valine (V), lysine (L), isoleucine (I), serine (S) or threonine (T); or
   (f) ALYSFLLDFV (SEQ ID NO: 22),
   and wherein the polypeptide is not more than twelve amino acids in length.

2. The isolated polypeptide of claim 1, comprising the amino acid sequence set forth as SX$_2$YX$_3$SLX$_4$SX$_5$ (SEQ ID NO: 18), wherein X$_2$ and X$_5$ are either a valine or a leucine, wherein X$_3$ is proline (P), serine (S), threonine (T), leucine (L), or valine (V) and wherein X$_4$ is tryptophan (W), valine (V), leucine (L), isoleucine (I), serine (S) or threonine (T).

3. The isolated polypeptide of claim 1, comprising the amino acid sequence set forth as WLLX$_6$GTSTX$_7$ (SEQ ID NO: 19), wherein X$_6$ is serine (S), threonine (T), isoleucine (I), or valine (V) and wherein X$_7$ is leucine (L) or valine (V).

4. The isolated polypeptide of claim 1, comprising the amino acid sequence set fourth as X$_8$LIASWTPV (SEQ ID NO: 20), wherein X$_8$ is one of tyrosine (Y) or tryptophan (W).

5. The isolated polypeptide of claim 1, comprising the amino acid sequence set forth as X$_9$LIASX$_{10}$TPV (SEQ ID NO: 21), wherein X$_9$ is an arginine (R), tyrosine (Y) or tryptophan (W) and X$_{10}$ is a valine (V), lysine (L), isoleucine (I), serine (S) or threonine (T).

6. The isolated polypeptide of claim 1, comprising the amino acid sequence set forth as ALYSFLLDFV (SEQ ID NO: 22).

7. The isolated polypeptide of claim 1, comprising the amino acid sequence set forth as WLLPGTSTX$_1$ (SEQ ID NO: 3), wherein X$_1$ is a leucine.

8. The isolated polypeptide of claim 1, wherein the polypeptide consists of the amino acid sequence set forth as one of:
   (a) WLLPGTSTX$_1$ (SEQ ID NO: 3), wherein X$_1$ is a leucine (L) or a valine (V);
   (b) SX$_2$YX$_3$SLX$_4$SX$_5$ (SEQ ID NO: 18), wherein X$_2$ and X$_5$ are either a valine or a leucine, wherein X$_3$ is proline (P), serine (S), threonine (T), leucine (L), or valine (V) and wherein X$_4$ is tryptophan (W), valine (V), leucine (L), isoleucine (I), serine (S) or threonine (T);
   (c) WLLX$_6$GTSTX$_7$ (SEQ ID NO: 19), wherein X$_6$ is serine (S), threonine (T), isoleucine (I), or valine (V) and wherein X$_7$ is leucine (L) or valine (V);
   (d) X$_8$LIASWTPV (SEQ ID NO: 20, wherein X$_8$ is one of tyrosine (Y) or tryptophan (W);
   (e) X$_9$LIASX$_{10}$TPV (SEQ ID NO: 21), wherein X$_9$ is an arginine (R), tyrosine (Y) or tryptophan (W) and X$_{10}$ is a valine (V), lysine (L), isoleucine (I), serine (S) or threonine (T); and
   (f) ALYSFLLDFV (SEQ ID NO: 22).

9. The isolated polypeptide of claim 1, wherein the polypeptide is eleven amino acids in length.

10. The isolated polypeptide of claim 1, wherein the polypeptide is nine or ten amino acids in length.

11. An isolated polypeptide, comprising the amino acid sequence set forth as WLLPGTSTX$_1$ (SEQ ID NO: 3), wherein X$_1$ is a valine and wherein the polypeptide is not more than 12 amino acids in length.

12. The isolated polypeptide of claim 11, wherein the polypeptide consists of the amino acid sequence set forth as SEQ ID NO: 3, wherein amino acid $X_1$ is a valine (V).

13. The isolated polypeptide of claim 11, wherein the polypeptide consists of the amino acid sequence set forth as SEQ ID NO: 3, wherein amino acid $X_1$ is a leucine.

14. An isolated polynucleotide encoding the polypeptide of claim 1, wherein the polynucleotide does not encode more than twelve amino acids of SEQ ID NO: 1.

15. The polynucleotide of claim 14, operably linked to a promoter.

16. A vector comprising the polynucleotide of claim 15.

17. The vector of claim 16, wherein the vector is a plasmid vector.

18. The vector of claim 17, wherein the plasmid vector is expressed in *Salmonella*.

19. The vector of claim 17, wherein the plasmid vector is expressed in yeast.

20. The vector of claim 16, wherein the vector is a viral vector.

21. The vector of claim 20, wherein the vector is a retrovirus, orthopox, avipox, fowlpox, capripox, suipox, adenoviral, herpes virus, alpha virus, baculovirus, Sindbis virus, vaccinia virus or poliovirus vector.

22. The vector of claim 16, wherein the vector encodes the amino acid sequence set forth as SEQ ID NO: 3, wherein amino acid $X_1$ is a leucine (L).

23. An isolated host cell comprising the vector of claim 17.

24. The isolated host cell of claim 23, wherein the host cell is a yeast cell.

25. A composition comprising a first recombinant virus which has incorporated into a viral genome or infectable portion thereof a nucleic acid encoding the isolated polypeptide of claim 1 and a second recombinant virus which has incorporated into a viral genome or infectable portion thereof one or more genes or DNA sequences encoding a costimulatory molecule, wherein the composition is able to coinfect a host cell resulting in coexpression of the polypeptide and the genes or DNA sequences encoding the costimulatory molecule.

26. The composition of claim 25, wherein the costimulatory molecule is one or more of B7-1, B7-2, LFA-3 or ICAM-1.

27. The composition of claim 25, comprising the first and second viruses in amounts effective to ameliorate a disease in a mammal.

28. The composition of claim 25, wherein the first recombinant virus, the second recombinant virus, or the first and second recombinant viruses is selected from the group consisting of retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors.

29. The composition of claim 25, wherein the second recombinant virus further comprises one or more exogenous DNA sequences encoding one or more immunostimulatory molecules, wherein the immunostimulatory molecule is selected from the group consisting of IL-2, ICAM-1, LFA-3, CD72, GM-CSF, TNF-α, IFN-γ, IL-12, and IL-6 or wherein the composition further comprises an effective amount of at least one of an exogenous immunostimulatory molecule selected from the group consisting of IL-2, GM-CSF, TNF-α, IL-12, and IL-6.

30. The composition of claim 25, wherein the first recombinant virus, the second recombinant virus, or the first and second recombinant virus is vaccinia virus.

31. A pharmaceutical composition comprising the composition of claim 25 and a pharmaceutically acceptable carrier.

32. A pharmaceutical composition comprising a therapeutically effective amount of the host cell of claim 23 in a pharmaceutically acceptable carrier.

33. A pharmaceutical composition comprising a therapeutically effective amount of the polypeptide of claim 1 in a pharmaceutically acceptable carrier.

34. A method for eliciting an immune response in a subject, comprising administering to a subject a therapeutically effective amount of the polypeptide of claim 1, or a polynucleotide encoding the polypeptide, thereby producing an immune response in the subject.

35. The method of claim 34, further comprising administering an adjuvant to the subject.

36. The method of claim 34, further comprising administering to the subject a therapeutically effective amount of IL-2, RANTES, GM-CSF, TNF-α, IFN-γ, G-CSF or a combination thereof, or administering to the subject a nucleic acid molecule encoding one or more of IL-2, RANTES, GM-CSF, TNF-α, IFN-γ, G-CSF, LFA-3, CD72, B7-1, B7-2, OX-40L, 4-1 BBL and ICAM-1.

37. A method of detecting T cells expressing CD8 that specifically recognize SEQ ID NO: 1 in a subject, comprising contacting peripheral blood mononuclear cells isolated from the subject with a reagent comprising the polypeptide of claim 1; and detecting the presence of the polypeptide bound to the peripheral blood mononuclear cells, thereby detecting T cells expressing CD8 that specifically bind SEQ ID NO: 1.

38. The method of claim 37, further comprising contacting the peripheral blood mononuclear cells with an additional reagent.

39. The vector of claim 22, wherein the vector does not encode SEQ ID NO:1.

40. A method for eliciting an immune response in a subject, comprising administering to a subject a therapeutically effective amount of the polypeptide of claim 11, or a polynucleotide encoding the polypeptide, thereby producing an immune response in the subject.

41. The method of claim 40, further comprising administering an adjuvant to the subject.

42. The method of claim 40, further comprising administering to the subject a therapeutically effective amount of IL-2, RANTES, GM-CSF, TNF-α, IFN-γ, G-CSF or a combination thereof, or administering to the subject a nucleic acid molecule encoding one or more of IL-2, RANTES, GM-CSF, TNF-α, IFN-γ, G-CSF, LFA-3, CD72, B7-1, B7-2, OX-40L, 4-1 BBL and ICAM-1.

* * * * *